US010774323B2

(12) United States Patent
Urban et al.

(10) Patent No.: US 10,774,323 B2
(45) Date of Patent: Sep. 15, 2020

(54) METHODS FOR DISPLAYING CYCLIC PEPTIDES ON BACTERIOPHAGE PARTICLES

(71) Applicant: LanthioPep B.V., Groningen (NL)

(72) Inventors: Johannes Herbert Urban, Munich (DE); Markus Andreas Moosmeier, Landau a.d. Isar (DE); Tjibbe Bosma, HP Lippenhuizen (NL); Josef Prassler, Germering (DE)

(73) Assignee: LANTHIOPEP B.V., Groningen (NL)

( * ) Notice: Subject to any disclaimer, the term of this patent is extended or adjusted under 35 U.S.C. 154(b) by 0 days.

(21) Appl. No.: 15/537,910

(22) PCT Filed: Dec. 21, 2015

(86) PCT No.: PCT/EP2015/080738
§ 371 (c)(1),
(2) Date: Jun. 20, 2017

(87) PCT Pub. No.: WO2016/102434
PCT Pub. Date: Jun. 30, 2016

(65) Prior Publication Data
US 2018/0051276 A1 Feb. 22, 2018

(30) Foreign Application Priority Data

Dec. 22, 2014 (EP) ...................... 14199588

(51) Int. Cl.
*C12N 15/10* (2006.01)
*C07K 7/06* (2006.01)
*C07K 7/08* (2006.01)
*C07K 7/50* (2006.01)
*C07K 11/02* (2006.01)

(52) U.S. Cl.
CPC ............ *C12N 15/1037* (2013.01); *C07K 7/06* (2013.01); *C07K 7/08* (2013.01); *C07K 7/50* (2013.01); *C07K 11/02* (2013.01)

(58) Field of Classification Search
None
See application file for complete search history.

(56) References Cited

U.S. PATENT DOCUMENTS

| 2013/0184177 A1 | 7/2013 | Tjibbe .............................. 506/9 |
| 2017/0204400 A1* | 7/2017 | van der Donk .... C12N 15/1037 |

FOREIGN PATENT DOCUMENTS

| WO | WO1988/06630 | 9/1988 |
| WO | WO1990/02809 | 3/1990 |
| WO | WO2000/077194 | 12/2000 |
| WO | WO2006/062398 | 6/2006 |
| WO | WO2009/098450 | 8/2009 |
| WO | WO2012/005578 | 1/2012 |
| WO | WO2012/019928 | 2/2012 |
| WO | 2013051938 | 4/2013 |

OTHER PUBLICATIONS

Sidhu Biomol. Eng. 18:57-63 (Year: 2001).*
Plat et al (Applied and Environmental Microbiology 77:604-11) (Year: 2011).*
Angelini, et al. "Post-translational modification of genetically encoded polypeptide libraries" (2011) Current Opinion in Chemical Biology 15, 355-361.
Bass, et al. "Hormone phage: an enrichment method for variant proteins with altered binding properties" (1990) Proteins: Structure, Function, and Bioinformatics 8(4):309-14.
Bhat, et al. "Lead discovery and optimization strategies for peptide macrocycles" (2014) European Journal of Medicinal Chemistry 5223-5234.
Dunn "Phage display of proteins" (1996) Curr. Opin. Biotechnol. 7(5):547-53.
Frost, et al. "Design, synthesis, and diversification of ribosomally derived peptide macrocycles" (2013) Curr. Opin. Struct. Biol. 23 (4), 571-580.
Fuh, et al. "Efficient phage display of polypeptides fused to the carboxy-terminus of the M13 gene-3 minor coat protein" (2000) Febs Letters 480, 231-234.
Gao, et al. "Making artificial antibodies: A format for phage display of combinatorial heterodimeric arrays" (1999) Proc Natl Acad Sci U S A 96, 6025-6030.
Giebel, et al. "Screening F Cyclic Peptide Phage Libraries Identifies Ligands That Bind Streptavidin With High Affinities" (1995) American Chemical Society 34 (47), pp. 15430-15435.
Greenwood, et al. "Multiple display of foreign peptides on a filamentous bacteriophage. Peptides from Plasmodium falciparum circumsporozoite protein as antigens" (1991) J Mol Biol. 20;220(4):821-7.
Held et al. "Comprehensive Mutational Analysis of the M13 Major Coat Protein: Improved Scaffolds for C-terminal Phage Display" (2004) Journal of Molecular Biology 340, 587-597.
Jespers, et al. "Surface expression and ligand-based selection of cDNAs fused to filamentous phage gene VI" (1995) Nature Medicine 2, 299-305.
Kay, et al. "Phage display of peptides and proteins: a laboratory manual", (1996) Biology of the filamentous bacteriophage. Academic Press. San Diego, pp. 1-20.
Knerr and van der Donk, "Discovery, biosynthesis, and engineering of lantipeptides" (2012) Annu. Rev. Biochem. 81:479-505.
Kuipers, et al. "NisT, the transporter of the lantibiotic nisin, can transport fully modified, dehydrated, and unmodified prenisin and fusions of the leader peptide with non-lantibiotic peptides" (2004) J. Biol. Chem. 279, 22176-22182.
McGregor, "Selection of proteins and peptides from libraries displayed on filamentous bacteriophage" (1996) Mol. Biotechnol. 6, 155-162.
Parmley & Smith, "Antibody-selectable filamentous fd phage vectors: affinity purification of target genes" (1988) Gene 73(2):305-18.

(Continued)

Primary Examiner — Christopher M Gross
(74) Attorney, Agent, or Firm — Licata & Tyrrell P.C.

(57) ABSTRACT

The present invention relates to methods for displaying cyclic peptides on the surface of bacteriophage particles and collections thereof.

6 Claims, 5 Drawing Sheets

Specification includes a Sequence Listing.

(56) References Cited

OTHER PUBLICATIONS

Smith, "Filamentous fusion phage: Novel expression vectors that display cloned antigens on the virion surface" (1985) Science 228, 1315-1317.
Tjibbe, et al. "Bacterial Display and Screening of Posttranslationally Thioether-Stabilized Peptides" (2011) Applied and Environmental Microbiology, American Society for Microbiology 77, 6794-6801.
Van Der Donk and Oman, "Follow the leader: the use of leader peptides to guide natural product biosynthesis" (2010) Nature Chemical Biology 6, 9-18.
Van der Donk, et al. "Structure and mechanism of lanthipeptide biosynthetic enzymes" (2014) Current Opinion in Structural Biology 29:58-66.
Weiss, et al. "Design and evolution of artificial M13 coat proteins" (2000) Journal of Molecular Biology 300, 213-219.
International Search Report and Written Opinion in PCT/EP2015/080738 dated Mar. 4, 2016.
International Preliminary Report on Patentability in PCT/EP2015/080738 dated Jun. 27, 2017.
First Office Action in Chinese Patent Application No. 201580069979.0 dated Apr. 1, 2020 with English Language Translation.
Plat et al. "Requirements of the Engineered Leader Peptide of Nisin for Inducing Modification, Export and Cleavage" Applied and Environmental Microbiology 2011 77(2):604-611.
Sidhu, S.S. "Engineering M13 for phage display" Biomolecular Engineering 2001 18:57-63.
Zhang et al. "Evolution of lanthipeptide synthetases" PNAS 2012 109(45):18361-18366.
Pande et al. "Phage display: Concept, innovations, applications and future" Biotechnology Advances 2010 28:849-858.
Weiz, A.R. "Characterization and manipulation of the biosynthetic pathway of cyanobacterial tricyclic microviridins in *E. coli*" 2012 pp. 1-158.

\* cited by examiner

Figure 2
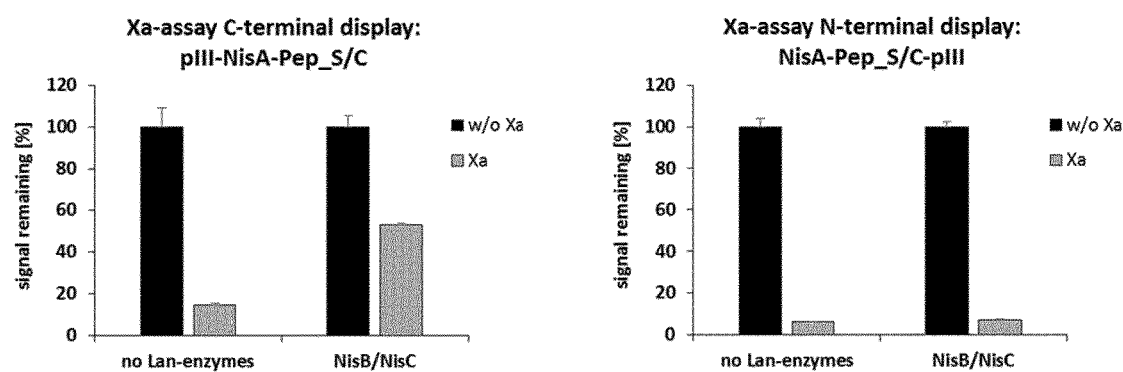
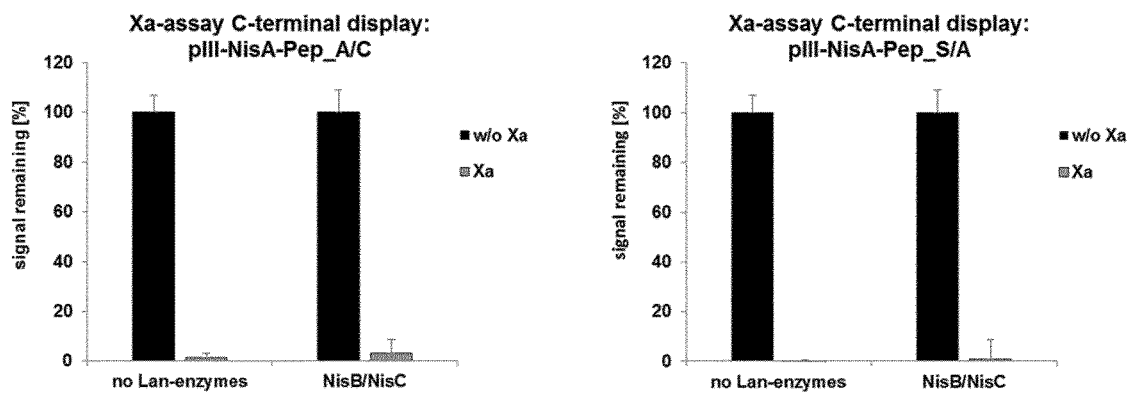
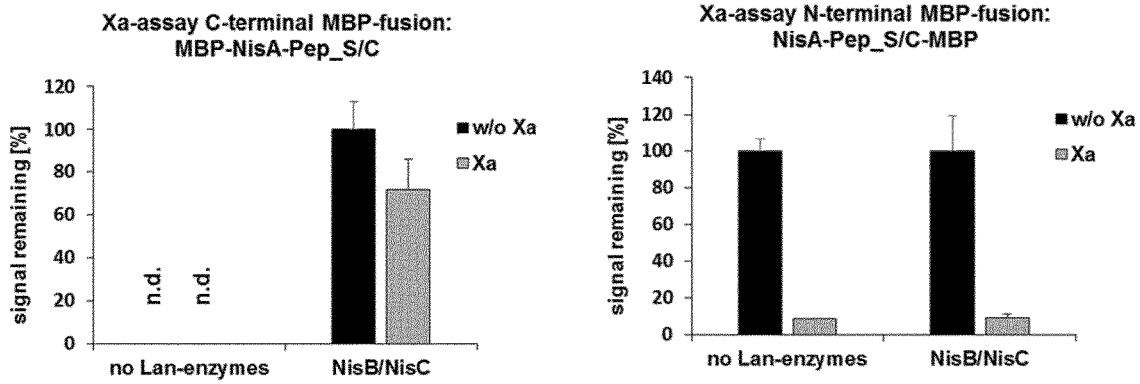

Figure 4 pIII  MKKLLFAIPLVVPFYSHSAETVESCLAKPHTENSFTNVWKDDKTLDRYANYEGCLWNA
TGVVVCTGDETQCYGTWVPIGLAIPENEGGGSEGGGSEGGGSEGGGTKPPEYGDTPIP
GYTYINPLDGTYPPGTEQNPANPNPSLEESQPLNTFMFQNNRFRNRQGALTVYTGTVT
QGTDPVKTYYQYTPVSSKAMYDAYWNGKFRDCAFHSGFNEDPFVCEYQGQSSDLPQPP
VNAGGGSGGGSGGGSEGGGSEGGGSEGGGSEGGGSGGGSGSGDFDYEKMANANKGAMT
ENADENALQSDAKGKLDSVATDYGAAIDGFIGDVSGLANGNGATGDFAGSNSQMAQVG
DGDNSPLMNNFRQYLPSLPQSVECRPFVFSAGKPYEFSIDCDKINLFRG**VFAFLLYVA
TFMYVFSTFANILRNKES pVIII MKKSLVLKASVAVATLVPMLSFAAEGDDPAKAAFNSLQASATEYIGYAWAMVVVIVGA
TIGIKLFKKF**TSKAS

Figure 5
A
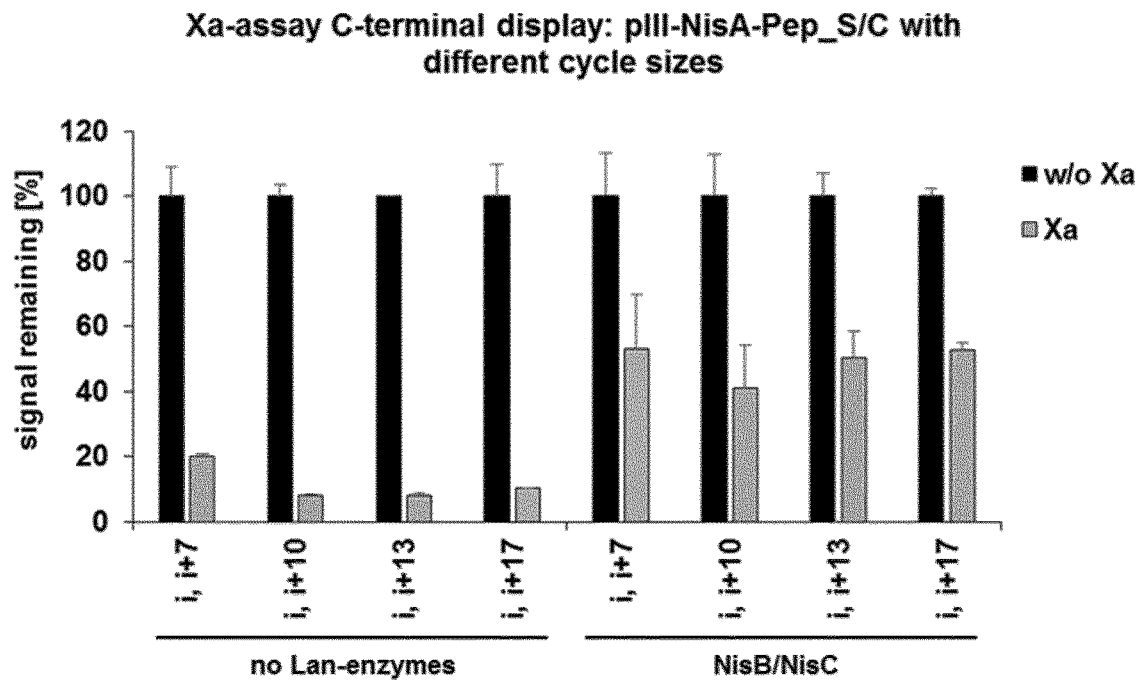
B
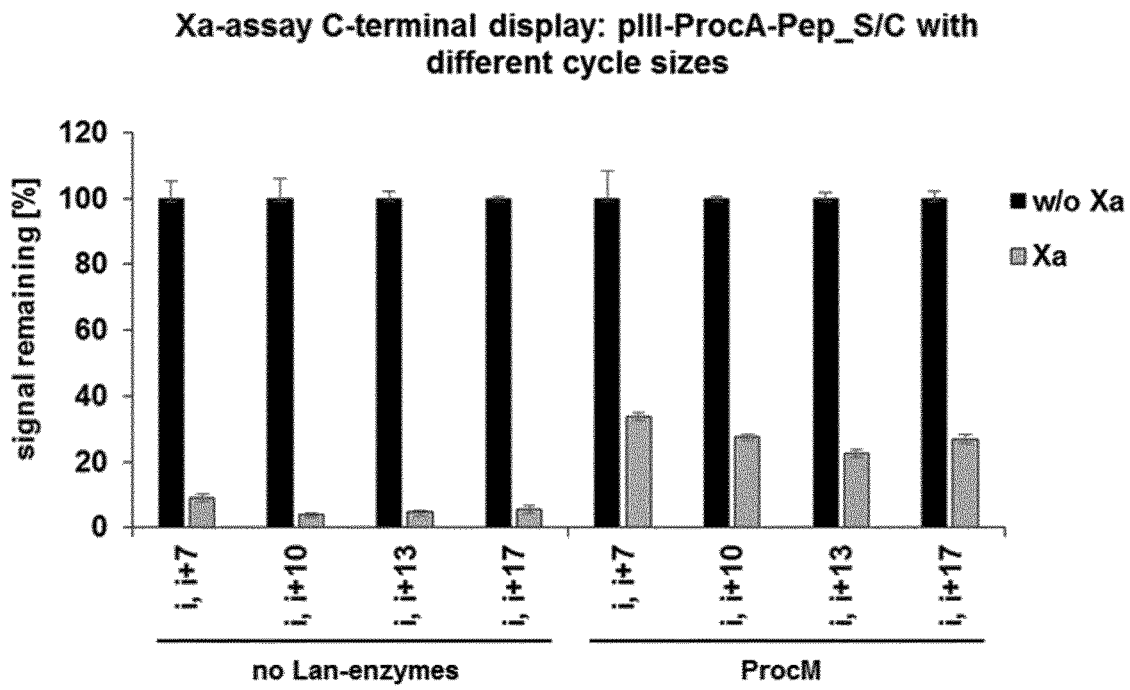

METHODS FOR DISPLAYING CYCLIC PEPTIDES ON BACTERIOPHAGE PARTICLES

This patent application is the National Stage of International Application No. PCT/EP2015/080738 filed Dec. 21, 2015, which claims the benefit of EP 14199588.6 filed Dec. 22, 2014 each of which is incorporated by reference in its entirety.

FIELD OF THE INVENTION

The present invention relates to methods for displaying cyclic peptides on the surface of bacteriophage particles at the C-terminus of a phage coat protein.

BACKGROUND OF THE INVENTION

Cyclic peptides are polypeptide chains taking cyclic ring structure and are known to have multiple biological activities, such as antibacterial activity, immunosuppressive activity or anti-tumor activity. Several cyclic peptides found in nature are used in the clinic such as the anti-bacterials gramicidin S, tyrocidine, and vancomycin, or cyclosporine A having immunosuppressive activity. Encouraged by natural cyclic peptides with biological activity, efforts have been made to develop artificial cyclic peptides with both genetic and synthetic methods.

An emerging class of biomolecules having cyclic structure are ribosomally synthesized peptides, which require extensive post translational modification to form the biologically active peptide. Most ribosomally synthesized natural peptides are translated as precursors composed of a leader- and a core-peptide. The leader serves as recognition sequence and recruits the enzymatic machinery to install post-translational modifications (PTMs) at specific residues of the core peptide.

Thereby the post-translational modifications, such as hetero- or macrocyclization, dehydration, acetylation, glycosylation, halogenation, prenylation, and epimerization not only emerge the biological activity of such peptides but also directly contribute to the excellent stability found in many representative members of this peptide class, and thus makes them attractive candidates for drug development.

Lanthipeptides and lantibiotics form a group of unique ribosomally synthesised and post-translationally modified antibiotic peptides that are produced by, and primarily act on, Gram-positive bacteria (for review see Knerr and van der Donk, Annu. Rev. Biochem. 2012. 81:479-505). Natural lantibiotics, such as e.g. nisin or subtilin are well studied and commercially used in the food industry for making and preserving dairy products such as cheese.

Lanthipeptides and lantibiotics as a subclass of peptides with antimicrobial activity, contain intramolecular thioether-bridges or rings formed by the thioether amino acids lanthionine (Lan) and 3-methyllanthionine (MeLan) which protect such peptides against proteolytic degradation and confer increased thermostability. Thioether-bridge installment starts with the enzymatic dehydration of serine or threonine to the unsaturated dehydroalanine (Dha) and dehydrobutyrine (Dhb), respectively, followed by intramolecular Michael-type addition of cysteine thiols and are mediated by lanthipeptide synthetases (LanB and LanC for class I, LanM for class II, LanKC for class III, and LanL for class IV). In class I lanthipeptides, serine/threonine dehydration and subsequent cyclisation are performed by a LanB type dehydratase and a LanC type cyclase, respectively, whereas in class II lanthipeptides a single bifunctional LanM type enzyme performs both reactions. Interestingly, unsaturated Dha has a high chemical reactivity and can, under mild basic conditions, readily react with the side of cysteine or lysine to yield non-stereoselective thioether-bridges and lysinoalanine-bridges, respectively. The biosynthesis of class III and class IV lanthipeptides is supported by multifunctional LanKC and LanL type enzymes, respectively, which are characterized by an amino-terminal phospho-Ser/phospho-Thr lyase domain, a central kinase-like domain, and a carboxy-terminal LanC-like domain (cyclase) (van der Donk et al. 2014 Current Opinion in Structural Biology 2014, 29:58-66).

Over the last years the principle of lanthipeptide biosynthesis was more and more adapted for the discovery and generation of artificial bioactive peptides having cyclic structure.

First in 2004 it has been proposed that the lanthipeptide-synthesizing enzymes can be advantageously used to introduce PTMs, such as thioether-bridges, into peptides that are normally unmodified, to improve the stability of the peptide and/or to alter its activity (Kuipers et al. 2004. J. Biol. Chem. 279, 22176-22182). In WO2006/062398 it was shown that a peptide of interest can be dehydrated in a host cell by an isolated lantibiotic dehydratase, such as LanB, which is not part of the conventional lantibiotic enzyme complex. It was further demonstrated that modified thioether-bridge containing peptides can be secreted by a protein export system other than the dedicated lantibiotic transporters in its natural host.

Later, in WO2012/005578 it was demonstrated that thioether-bridge containing peptides could readily be produced by, and displayed on, the surface of a host cell (e.g. *Lactococcus lactis*) which expresses the biosynthetic and export machinery for lantibiotics.

More specifically, WO2012/005578 provides an expression vector encoding a fusion peptide comprising an N-terminal lantibiotic leader sequence, an amino acid sequence of interest to be post-translationally modified to a dehydroresidue- or thioether-containing polypeptide and a C-terminal charged membrane anchoring domain. Also a display library to screen for cyclized peptides with a desired activity was suggested. However, only display on Gram-positive host cells, in particular lactic acid bacteria, which by nature are able to produce lantibiotics was enabled.

Other display systems known in the art such as phage display that require gram-negative bacteria having a different protein export machinery were not considered as an alternative and therefore were not enabled in the prior art.

The story of phage display started in 1985 based on the demonstration that filamentous phage tolerate foreign protein fragments inserted in their gene III protein (pIII) and also present the protein fragments on the phage surface (Smith, 1985). Ladner extended that concept to the screening of repertoires of (poly)peptides and/or proteins displayed on the surface of phage (WO1988/06630; WO1990/02809) and, since then, phage display has experienced a dramatic progress and resulted in substantial achievements. Various formats have been developed to construct and screen (poly) peptide/protein phage-display libraries, and a large number of review articles and monographs cover and summarise these developments (e.g., Kay et al., 1996; Dunn, 1996; McGregor, 1996). To anchor the peptide or protein to the filamentous bacteriophage surface, mostly genetic fusions to phage coat proteins are employed. Preferred are fusions to gene III protein (Parmley & Smith, 1988) or fragments thereof (Bass et al., 1990), and gene VIII protein (Greenwood et al., 1991). In one case, gene VI has been used (Jespers et al., 1995), and recently, a combination of gene VII and gene IX has been used for the display of Fv fragments (Gao et al., 1999).

So far only linear (poly) peptides and cyclic peptides stabilized via disulphide bonds were successfully displayed on phages (see WO2000/077194, WO2009/098450). More recently in WO2012/019928 the linear precursor of Microvividrin K fused to the N-terminus of the pIII was displayed on phage. The post-translational modification of the displayed linear precursor was achieved by subsequent incubation of the phages with cell lysates containing the cognate modifying enzymes. However, WO2012/019928 does not provide enabling disclosure for the display of lanthipeptides and also does not teach the display of peptides which underwent post-translational modification prior to phage assembly.

Accordingly, a need exists to translate the display of cyclic post-translationally modified peptides from bacteria to classic phage display.

SUMMARY OF THE INVENTION

In the prior art display of thioether-bridge containing peptides on bacteria was successfully demonstrated. However, significant disadvantages are accompanied with the use of bacteria for display. For example, gram-positive bacteria, such as *L. lactis*, have a reduced transformation efficiency in terms of electroporation and have a tendency for clumping which makes its handling difficult and results unsteady. Therefore, libraries displayed via *L. lactis*, could not exceed diversities beyond ~$10^6$ whereas typical phage display libraries are known to have more than $10^{12}$ distinct clones.

The technical problem underlying the present disclosure is therefore to develop a simple, reliable system which enables the presentation of cyclic peptides on phage particles. The solution to this technical problem is achieved by providing the embodiments characterised herein. The present disclosure attaches the cyclic peptide to the C-terminus of a phage coat protein and enables display of said cyclic peptides on the phage surface. C-terminal phage display as such was shown for linear peptides on the pVIII (Held et al., 2004 & Weiss et al., 2000) and also on the pIII coat proteins (Fuh et al., 2000) but the display of a cyclic peptide or post-translationally modified peptide via the C-terminus of a phage coat protein was neither mentioned nor suggested. Generally, conventional phage display uses the N-terminus of a phage coat protein for display and it was not expected that cyclic peptides could be displayed effectively only via the C-terminus of a phage coat protein.

More specifically the present disclosure comprises a method for displaying a cyclic peptide on a bacteriophage particle, the method comprising the following steps:

(a) providing a host cell harbouring a nucleic acid sequence encoding a precursor cyclic peptide;

(b) causing or allowing the expression of said precursor cyclic peptide;

(c) enzymatic dehydration of one or more amino acid residues within the precursor cyclic peptide;

(d) forming one or more intramolecular bonds by coupling of one or more dehydrated residues to a cysteine or a lysine, thereby forming a cyclic peptide; and (e) producing bacteriophage particles in said host cell, wherein said bacteriophage particles display said cyclic peptide on the surface and wherein said cyclic peptide is attached to the C-terminus of a coat protein of said bacteriophage particles.

In one aspect the cyclic peptide comprises an intramolecular bond formed by coupling of one or more dehydrated residues to a cysteine or a lysine. In another aspect the cyclic peptide comprises an intramolecular bond formed by coupling of one or more dehydrated residues to a cysteine residue or a lysine residue. In another aspect the cyclic peptide comprises an intramolecular bond formed by coupling of one or more dehydrated amino acid residues to a cysteine or a lysine.

Accordingly, the present disclosure allows to present cyclic peptides on phage. The technical approach of the present disclosure, i.e. attaching the cyclic peptides to the C-terminus of a phage coat protein, is neither provided nor suggested by the prior art.

Thus, the present disclosure relates to a method for displaying a cyclic peptide on the surface of a bacteriophage particle, wherein said cyclic peptide is attached to the C-terminus of a coat protein of said bacteriophage particle. Additionally, the present disclosure allows creating and screening large libraries of cyclic peptides displayed on the surface of bacteriophage particles.

In many cases it is advantageous to present cyclic peptides using such method. There is utility in the claimed method to display a library comprising cyclic peptides.

Furthermore, there is utility in a library comprising cyclic peptides displayed by using the claimed method. Such libraries comprise a wide range of cyclic peptides that can be screened against a target of interest.

Utilization of the disclosed methods makes it possible to introduce an intramolecular bond at essentially any desired position in a peptide. Of particular interest are peptides with a biological activity, e.g. peptides intended for therapeutic use, because the introduction of one or more intramolecular bonds generally increases the biostability of the peptide. Furthermore, a cyclic structure may be used to alter the biological activity, for instance antigen specificity, receptor binding affinity, antimicrobial activity, or enzyme specificity of a peptide. The peptide of interest is for example an agonistic peptide, an antagonistic peptide, an amidated peptide, a hormone, an enzyme inhibitor, an enzyme activator, a receptor ligand, an inhibitory peptide, a lantibiotic protein, a viral protein, a eukaryotic protein, a mutant thereof (e.g. specifically designed to allow for a modification at a certain position), a mimic, a homologue or a functional fragment equivalent thereof. Such method can be used to identify therapeutically relevant and therapeutically active molecules based on cyclic peptides, or can be used to characterize such molecules.

Figure 1:
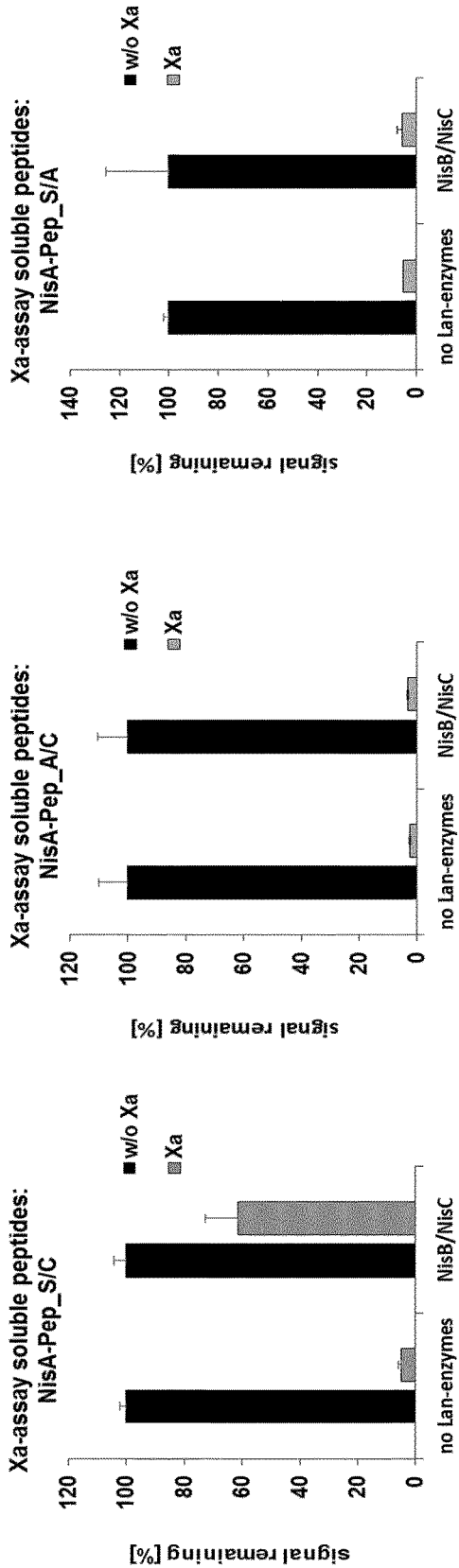
FIG. 1: Factor Xa-cleavage reporter assays confirm the modification status of cyclic peptides expressed in *E. coli*.

The modification status of soluble expressed peptides harboring a NisA-leader sequence was assessed in *E. coli* cell lysates in presence or absence of co-expression of the modifying NisB/NisC enzymes using ELISA-based Factor Xa-cleavage reporter assays. While peptides containing an ASWIEGRWCN-motif (SEQ-ID.: 1; Factor Xa recognition sequence underlined) produced in the absence of NisB/NisC co-expression (no Lan-enzymes) are almost cleaved to completion by Factor Xa, co-expression of NisB/NisC leads to the enzymatic introduction of a thioether-bridge from dehydroalanine (dehydrated serine) to cysteine and Factor Xa-cleavage resistance (left panel). Mutating either the serine (middle panel) or cysteine (right panel) residues to alanine prevents enzymatic thioether-bridge formation even in presence of NisB/NisC co-expression and renders the peptides Factor Xa-sensitive. The Factor Xa resistance (signal remaining [%]) was calculated relative to untreated samples (w/o Xa) from three independently produced cell-lystes.

FIG. 2: Fusions of NisA-leader containing precursor peptides to the C-terminus of pIII are substrates for enzymatic cyclization (thioether-bridge formation) and are subsequently displayed on phage particles.

(A) Phage particles were produced using phagemids which fused the same NisA-leader containing peptide with an ASWIEGRWCN-motif (SEQ-ID.: 1) either to the C-terminus or N-terminus of pIII and subjected to Factor Xa-cleavage reporter assays. C-terminal fusions produced in the presence of NisB/NisC co-expression and displayed on phage are largely resistant to Factor Xa-cleavage indicating enzymatic modification in the producer cell and subsequent incorporation into phage particles (left panel). In contrast N-terminal fusions of the same peptide displayed on phage are Factor Xa-sensitive even when produced in presence of NisB/NisC co-expression (right panel). (B) Mutating either the serine (left panel) or cysteine (right panel) residues to alanine in the core peptides of the C-terminal pIII fusions prevents enzymatic thioether-bridge formation even in presence of NisB/NisC co-expression and renders the displayed peptides Factor Xa-sensitive. The Factor Xa resistance (signal remaining [%]) was calculated relative to untreated samples (w/o Xa) from three independently produced phage samples. (C) Cell lysates of *E. coli* strains expressing the same NisA-leader containing precursor peptide shown in (A) fused either to the C-terminus or N-terminus of the Maltose-binding protein (MBP) were produced and subjected to Factor Xa-cleavage reporter assays. Fusions of the precursor peptide to the C-terminus of MBP are largely Factor Xa-cleavage resistant when produced in the presence of NisB/NisC co-expression confirming enzymatic modification. In the absence of NisB/NisC co-expression the same peptide fusions could not be detected (n.d.) which might indicate rapid turnover (left panel). N-terminal fusions of the precursor peptide to MBP accumulated to high levels regardless of NisB/NisC co-expression, but fail to be enzymatically modified as judged by Factor Xa-cleavage assays (right panel). The results suggest that fusion of precursor peptides to the C-terminus of carrier proteins is widely applicable and, in contrast to N-terminal fusion, supports efficient modification by the enzymatic machinery.

Figure 3:
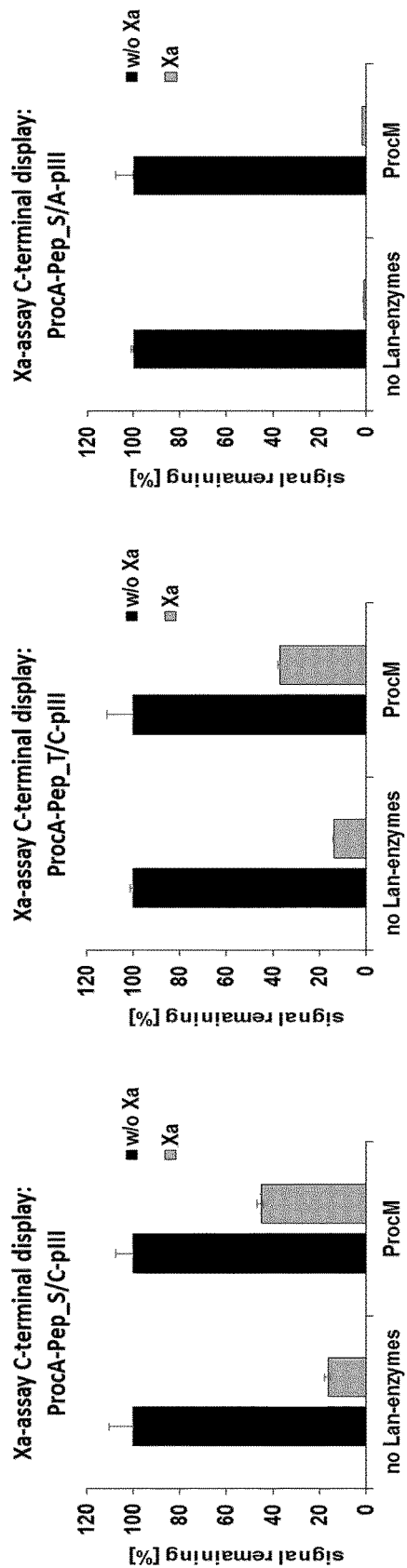

FIG. 3: Fusions of ProcA-leader containing precursor peptides to the C-terminus of pIII are substrates for enzymatic cyclization (thioether-bridge formation) and are subsequently displayed on phage particles.

Phage particles were produced using phagemids which fused a ProcA-leader containing peptide with an ASWIEGRWCN-motif (SEQ-ID.: 1; S/C; or cognate T/C and S/A derivatives) to the C-terminus of pIII and subjected to Factor Xa-cleavage reporter assays. C-terminal peptide fusions containing either S/C (left panel) or T/C (middle panel) residues produced in the presence of ProcM enzyme co-expression show resistance to Factor Xa-cleavage indicating enzymatic thioether-bridge formation from dehydroalanine (S/C) and dehydrobutyrine (T/C), respectively, and subsequent incorporation into phage particles. In contrast fusions with S/A residues are no substrates for thioether formation and remain Xa-sensitive (right panel) even when produced in presence of ProcM. The Factor Xa resistance (signal remaining [%]) was calculated relative to untreated samples (w/o Xa) from three independently produced phage samples.

FIG. 4: Wild-type amino acid sequence of Enterobacteria phage M13 g3p (pIII) and g8p (pVIII) proteins The sequences of pIII (SEQ-ID.: 2; UniProt-ID: P69168) and pVIII (SEQ-ID.: 3; UniProt-ID: P69541) proteins are provided with the signal peptide (bold face) and transmembrane domain sequences (bold face, underlined) highlighted.

FIG. 5: Enzymatic cyclization (thioether-bridge formation) and phage display of peptide fusions containing NisA- and ProcA-leader sequences and variable cycle sizes on the C-terminus of pIII.

(A) Phage particles were produced using phagemids which fused NisA-leader containing peptides with either ASWIEGRECN—(SEQ-ID.: 11), ASWAAIEGRAECN—(SEQ-ID.: 12), ASWAAAIEGRAAAECN—(SEQ-ID.: 13), or ASWAAGAAIEGRAAGAAECN-motif (SEQ-ID.: 14) (constructs i,i+7, i,i+10, i,i+13, and i,i+17, respectively; Factor Xa cleavage site underlined) to the C-terminus of pIII and subjected to Factor Xa-cleavage reporter assays. C-terminal peptide fusions produced in the presence of NisB/C enzyme co-expression show resistance to Factor Xa-cleavage independent of the cycle size which is dictated by the Serine/Cysteine spacing. The Factor Xa resistance (signal remaining [%]) was calculated relative to untreated samples (w/o Xa) from three independently produced phage samples.

(B) Same as in (A), but pIII-peptide fusions containing the ProcA-leader sequence and produced in presence or absence of ProcM enzyme co-expression.

DEFINITIONS

The term "bacteriophage" refers to bacterial viruses forming packages consisting of a protein coat containing nucleic acid required for the replication of the phages. The nucleic acid may be DNA or RNA, either double or single stranded, linear or circular. Bacteriophage such as phage lambda or filamentous phage (such as M13, fd, or fl) are well known to the artisan of ordinary skill in the art. The term "bacteriophage particle" refers to the particles according to the present disclosure, i.e. to particles displaying a cyclic peptide. During the assembly of bacteriophages, the coat proteins may package different nucleic acid sequences, provided that they comprise a packaging signal.

The term "nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al. (1991) Nucleic Acid Res. 19:5081; Ohtsuka et al. (1985) J. Biol. Chem. 260: 2605-2608; and Rossolini et al. (1994) Mol. Cell. Probes 8:91-98). Specific nucleic acid sequences or vectors as disclosed herein have the ability to be packaged by bacteriophage coat proteins during assembly of bacteriophages or bacteriophage particles. Preferably said nucleic acid sequences or vectors are derived from naturally occurring genomes of bacteriophage, and comprise for example, in the case of filamentous phage, phage and phagemid vectors. The latter are plasmids containing a packaging signal and a phage origin of replication in addition to plasmid features.

The term "peptide" means a molecule having less than or equal to 50 amino acids.

The term "(poly)peptide" means a molecule having more than 50 amino acids consisting of one or more chains of multiple, i.e. two or more, amino acids linked via peptide bonds.

The term "protein" refers to (poly)peptides where at least part of the (poly)peptide has or is able to acquire a defined three-dimensional arrangement by forming secondary, tertiary, or quaternary structures within and/or between its (poly)peptide chain(s). This definition comprises proteins such as naturally occurring or at least partially artificial proteins, as well as fragments or domains of whole proteins, as long as these fragments or domains are able to acquire a defined three-dimensional arrangement as described above.

The terms "thioether" or "thioether-bridge" refers to a sulfur atom bonded to two different carbon or hetero atoms in a respective molecule. In one embodiment the thioether-bridge is formed after post-translational dehydration of one or more serine or threonine residues and coupling of said dehydrated residues to a cysteine. In one embodiment the thioether-bridge is a lanthionine- or a methyllanthionine-bridge. Lanthionine is a non-proteinogenic amino acid with the chemical formula (HOOC—CH($NH_2$)—$CH_2$—S—$CH_2$—CH($NH_2$)—COOH), composed of two alanine residues that are crosslinked on their β-carbon atoms by a thioether-bridge. Methyllanthionine is a non-proteinogenic amino acid with the chemical formula (HOOC—CH($NH_2$)—CH($CH_3$)—S—$CH_2$—CH($NH_2$)—COOH).

The term "lysinoalanine-bridge" refers to the interaction of dehydroalanine with a lysine residue. Herein the lysinoalanine-bridge is induced enzymatically or non-enzymatically, e.g. by adjustment of the pH. "Lysinoalanine" refers to the modified amino acid N6-(DL-2-amino-2-carboxyethyl)-L-lysine.

The term "intramolecular bond" as used herein refers to a covalent bonding between side chains of amino acids within a peptide sequence, without incorporating extramolecular (exogenous) structures and excluding chemical processing, such as disulfide bridge formation (e.g. through reduction reaction), cycloaddition or Staudinger reactions. Herein the intramolecular bond can be formed by coupling of one or more dehydrated residues to a cysteine or a lysine. In one embodiment said one or more dehydrated residues are dehydroalanines (Dha) or dehydrobutyrines (Dhb). Herein the intramolecular bond can be formed by a lysinoalanine-bridge or thioether-bridge. In one embodiment of the present disclosure the intramolecular bond is formed by a lanthionine-bridge. In another embodiment of the present disclosure the intramolecular bond is formed by a methyllanthionine-bridge. In an embodiment of the present disclosure one or more intramolecular bonds are formed within a peptide sequence. In an embodiment of the present disclosure the intramolecular bonds within a peptide sequence form a stabilizing ring structure. In one embodiment said one or more intramolecular bonds are formed enzymatically. In one embodiment said one or more intramolecular bonds are formed by a lanthipeptide synthetase. In one embodiment said one or more intramolecular bonds are formed by a cyclase. In one embodiment said cyclase is a LanC type cyclase, or a bifunctional LanM type enzyme or a multifunctional LanKC or LanL type enzyme. In another embodiment said LanC type cyclase is NisC (Uniprot accession number: Q03202), SpaC, MibC, PepC, EpiC or a functional equivalent thereof. In another embodiment said bifunctional LanM type enzyme is ProcM (Accession number NP_894083), LctM, MutM, BovM, LanM1/2, CinM, HalM1/2, CyanM1-4, or a functional equivalent thereof. In another embodiment said one or more intramolecular bonds are formed non-enzymatically. In a further embodiment said one or more intramolecular bonds are formed under basic conditions. In another embodiment said one or more intramolecular bonds are formed under mild basic conditions. In another embodiment said one or more intramolecular bonds are formed under basic conditions. In another embodiment said basic conditions are at pH7.5, pH8, pH8.5, pH9, pH9.5, pH10, pH10.5 pH11, pH11.5, pH12, pH12.5, pH13, pH13.5 or pH14. In a further embodiment said one or more intramolecular bonds are formed enzymatically, e.g. by a lanthipeptide synthetase and under basic conditions.

Herein the term "cyclic peptide" refers to a stretch of amino acids, a peptide or a polypeptide having a secondary structure formed by one or more intramolecular bonds. Not the entire stretch of amino acids or peptide or polypeptide needs to be circular. In an embodiment of the present disclosure a cyclic peptide is monocyclic or polycyclic peptide. In another embodiment a cyclic peptide comprises peptides such as naturally occurring or artificial peptides, as well as peptides that are fragments or domains of whole proteins. In a further embodiment a cyclic peptide is an amidated cyclic peptide.

The term "polycycle" or "polycyclic structure" refers to a structure having at least two, three, four or five intramolecular bonds. Depending on the length of the peptide as used according to the disclosure a more complex secondary peptide structure can be achieved.

The term "precursor cyclic peptide" refers to a stretch of amino acids, a peptide or a polypeptide that is capable to form a cyclic peptide according to the disclosure herein. More specifically a precursor cyclic peptide according to the present disclosure comprises at least one or more serines or threonines and one or more cysteines or lysines to form an intramolecular bond.

The term "dehydrated residue" refers to a modified amino acid residue that underwent a chemical reaction which involved the loss of a water molecule from the reacting molecule. In one embodiment the "dehydrated residue" is a dehydrated serine or a dehydrated threonine. In another embodiment the "dehydrated residue" is dehydroalanine (Dha) or dehydrobutyrine (Dhb). In one embodiment the dehydration of one or more serines or threonines is performed by a lanthipeptide synthetase. In one embodiment the dehydration of one or more serines or threonines is performed by a dehydratase. In one embodiment said enzymatic dehydration is performed by a LanB type dehydratase or by a bifunctional LanM type enzyme or a multifunctional LanKC or LanL type enzyme. In one embodiment said LanB type dehydratase is NisB (Uniprot accession number: P20103), EpiB, SpaB, MibB, PepB or a functional equivalent thereof. In another embodiment said bifunctional LanM type enzyme is ProcM (Accession number NP_894083), LctM, MutM, BovM, LanM1/2, CinM, HalM1/2, CyanM1-4, or a functional equivalent thereof.

The term "leader" or "leader sequence" as used herein shall refer to a recognition motif for a post-translationally modifying (PTM) enzyme. In an embodiment of the present disclosure the leader sequence is recognized by a post-translationally modifying (PTM) enzyme. In an embodiment of the present disclosure the leader sequence is a sequence which is recognized by a lanthipeptide synthetase. In another embodiment the leader sequence bears a consensus motif that can be derived from leader sequences which are recognized by a post-translationally modifying (PTM) enzyme. In another embodiment of the present disclosure the leader sequence is a sequence derived from a LanA precursor peptide. In another embodiment of the present disclosure the leader sequence bears a consensus motif that can be derived from a LanA precursor peptide. In another embodiment of the present disclosure the leader sequence is a sequence which is recognized by a LanB type dehydratase, a LanC type cyclase and/or a bifunctional LanM type enzyme or a multifunctional LanKC or LanL type enzyme.

The term "post-translationally modifying enzyme" or "PTM enzyme" as used herein shall refer to enzymes inducing structural changes of a translated peptide, e.g. specifically modifying natural ribosomal peptides in the biosynthesis of biologically active peptides as part of the processing machinery. This class includes multiple types of enzymes, including carboxylate-amine ligases, cyclases, dehydrogenases, cyclodehydratase decarboxylases, epimerases, hydroxylases, peptidases, dehydratases, lyases, kinases, transferases, esterases, oxygenases and isomerases, in particular lanthionine bond forming enzymes, cytolysin forming enzymes, cyanobactin forming enzymes, thiopeptide forming enzymes, conopeptide forming enzymes, microviridin forming enzymes, cyclotide forming enzymes, bacteriocin forming enzymes and subtilosin forming enzymes. Preferably, the PTM enzymes used herein are lanthipeptide synthetases. Preferably, the PTM enzymes used herein are dehydratases, cyclases or bi- or multifunctional enzymes comprising dehydratase or lyase/kinase and cyclase activity. More preferred the PTM enzymes used herein are LanB type dehydratases, LanC type cyclases, bifunctional LanM type enzymes or multifunctional LanKC or LanL type enzymes or a functional equivalent thereof.

The term "functional equivalent" of a peptide or protein means something that shares one or more, preferably substantially all, of the functions of that peptide or protein. Preferably, such functions are biological functions, preferably enzymatic functions, such as dehydratase and/or cyclase activity.

The term "surface of a bacteriophage particle" refers to the part of a bacteriophage particle which is in contact with the medium the particle is contained in and which is accessible. The surface is determined by the proteins being part of the phage coat (the members of the protein coat of the particle) which is assembled during phage production in appropriate host cells.

Phage display describes a selection technique in which a library of peptide or protein variants is expressed on the outside of a phage virion, while the genetic material encoding each variant resides on the inside. This creates a physical linkage between each variant protein sequence and the DNA encoding it, which allows rapid partitioning based on binding affinity to a given target molecule (antibodies, enzymes, cell-surface receptors, etc.) by an in vitro selection process called panning. In its simplest form, panning is carried out by incubating a library of phage-displayed peptides on a plate (or bead) coated with the target, washing away the unbound phage, and eluting the specifically bound phage. The eluted phages are then amplified and taken through additional binding/amplification cycles to enrich the pool in favor of binding sequences. After a few rounds, individual clones are characterized by DNA sequencing and ELISA.

The term "phagemid" refers to a plasmid vector having a bacterial origin of replication, e.g. CoIE 1, and a copy of an intergenic region of a bacteriophage. The phagemid may be based on any known bacteriophage including filamentous bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle (Sambrook et. al. 417).

The term "phage vector" refers to a double stranded replicative form of a bacteriophage containing a heterologous gene and capable of replication. The phage vector has a phage origin of replication allowing phage replication and phage particle formation. The phage is preferably a filamentous bacteriophage, such as, an M 13, fl, fd, Pf3 phage, or a derivative thereof, a lambdoid phage such as lambda, 21, phi80, phi81. 82, 424. 434, etc., or a derivative thereof, a Baculovirus or a derivative thereof, a T4 phage or a derivative thereof, a T7 phage virus or a derivative thereof. Preparation of DNA from cells means isolating the plasmid DNA from a culture of the host cells. Commonly used methods for DNA preparation are the large- and small-scale plasmid preparations described in sections 125-133 of Sambrook et al. After preparation of the DNA it can be purified by methods well known in the art such as that described in section 140 of Sambrook et al.

The term "coat protein" means a protein, or at least a portion thereof which is present on the surface of the bacteriophage particle. From a functional perspective, a coat protein is any protein which associates with a bacteriophage particle during the phage assembly process in a host cell, and remains associated with the assembled phage until it infects another host cell. In the case of filamentous bacteriophage, said wild type proteins are gene III protein (pIII), gene VI protein (pVI), gene VII protein (pVII), gene VIII protein (pVIII), and gene IX protein (pIX). The coat protein may be the major coat protein or may be a minor coat protein. A "major" coat protein is a coat protein which is present in the phage coat at 10 copies of the protein or more, e.g. major coat protein pVIII. A major coat protein may be present in tens, hundreds or even thousands of copies per phage. A minor coat protein is present in the phage coat at less than 10 copies per phage, e.g. minor coat protein pIII.

The term "wild type coat protein" refers to coat proteins forming the phage coat of naturally occurring bacteriophages. The sequences, including the differences between the closely related members of the filamentous bacteriophages such as fl, fd, and M13, are well known to one of ordinary skill in the art (see, e.g., Kay et al., 1996). In the case of filamentous bacteriophage, said wild type proteins are e.g. gene III protein (pIII), gene VI protein (pVI), gene VII protein (pVII), gene VIII protein (pVIII), and gene IX protein (pIX). In one embodiment, the present disclosure relates to a method, wherein said coat protein is a wild type coat protein of a bacteriophage.

In a further preferred embodiment, said coat protein is a truncated variant of a wild type coat protein of a bacteriophage, wherein said truncated variant comprises at least that part of said wild type coat protein causing the incorporation of said coat protein into the protein coat of the bacteriophage particle.

The term "truncated variant" refers to proteins derived from the wild type proteins referred to above which are modified by deletion of at least part of the wild type sequences. This comprises variants such as truncated gene III (pIII) or gene VIII (pVIII) protein variants which have been found in bacteriophage mutants (Crissman & Smith, 1984) or which have been generated in the course of standard phage display methods (e.g. Bass et al., 1990; Krebber, 1996). For example, said truncated variant may consist, or include, the CT domain of the gene III protein (pIII) or the gene VIII protein (pVIII). To identify truncated variants according to the present disclosure, a detection tag may be fused to the variant, and an assay may be set up to determine whether the variant is incorporated into the phage coat of bacteriophage particles formed in the presence of the variant.

In a yet further preferred embodiment, said coat protein is a modified variant of a wild type coat protein of a bacteriophage, wherein said modified variant is capable of being incorporated into the protein coat of the bacteriophage particle.

Methods for achieving modification of a wild type protein according to the present disclosure are well-known to one of ordinary skill in the art, and involve standard cloning and/or mutagenesis techniques. Methods for the construction of nucleic acid molecules encoding a modified variant of a wild type protein used in a method according to the present disclosure, for construction of vectors comprising said nucleic acid molecules, including the construction of phage and/or phagemid vectors, for introduction of said vectors into appropriately chosen host cells, for causing or allowing the expression of said modified protein are well-known in the art (see, e.g., Sambrook et al., 1989; Ausubel et al., 1999; Kay et al., 1996). To identify modified variants according to the present disclosure, a detection tag may be fused to the variant, and an assay may be set up to determine whether the variant is capable or being incorporated into the phage coat of bacteriophage particles formed in the presence of the variant.

Yet further preferred is a method, wherein said bacteriophage is a filamentous bacteriophage. Filamentous bacteriophage such as M13, fd, or fl are well known to the artisan of ordinary skill in the art.

In the case of filamentous bacteriophage, a method is particularly preferred, wherein said coat protein of the bacteriophage particle is or is derived from the wild type coat protein pIII.

Further preferred is a method, wherein said coat protein of the bacteriophage particle is or is derived from the wild type coat protein pIII. Preferably, those parts of the modified protein corresponding to the wild type protein exhibit an amino acid identity exceeding about 40%, preferably about 50%, preferably about 60%, preferably about 70%, preferably about 80%, most preferably about 90% compared to the corresponding wild type sequence.

The term "N-terminus" of a given polypeptide sequence is a contiguous length of the given polypeptide sequence that begins at or near the N-terminal residue of the given polypeptide sequence. An N-terminus of the given polypeptide can be defined by a length. Similarly, the term "C-terminus" of a given polypeptide sequence is a contiguous length of the given polypeptide sequence that ends at or near the C-terminal residue of the given polypeptide sequence. A C-terminus of the given polypeptide can be defined by a length. In one embodiment the present disclosure refers to the C-terminus of a coat protein. In a preferred embodiment the C-terminus of a coat protein is the amino acid or the amino acid sequence located C-terminal to the transmembrane domain of said coat protein. In another embodiment the C-terminus of a coat protein is the amino acid or the amino acid sequence located C-terminal to the transmembrane domain of said coat protein, wherein said coat protein is the gene III protein (pIII, SEQ-ID.: 2; Uniprot: P69168) or the gene VIII protein (pVIII; SEQ-ID.: 3; Uniprot: P69541). In one embodiment the C-terminus of the gene III protein (pIII) is the amino acid sequence LRNKES (SEQ-ID.: 4) or a derivate or modified variant thereof. In another embodiment the C-terminus of the gene III protein (pIII) is located C-terminal to the transmembrane domain and comprises one or more amino acids of the amino acid sequence LRNKES (SEQ-ID.: 4). In another embodiment the C-terminus of the gene VIII protein (pVIII) is the amino acid sequence TSKAS (SEQ-ID.: 5) or a derivate or modified variant thereof. In another embodiment the C-terminus of the gene VIII protein (pVIII) is located C-terminal to the transmembrane domain and comprises one or more amino acids of the amino acid sequence TSKAS (SEQ-ID.: 5). An overview scheme of the gene III protein (pIII) and the gene VIII protein (pVIII) is illustrated in FIG. 4.

In one embodiment of the present disclosure the C-terminus of the protein coat member is attached to the cyclic peptide and displays said cyclic peptide on the surface of a bacteriophage particle.

In a preferred embodiment, the bacteriophage particle displaying the (poly)peptide/protein contains a nucleic acid sequence encoding the (poly)peptide/protein.

In the context of the present disclosure, the term "causing or allowing the expression" describes cultivating host cells under conditions such that nucleic acid sequence is expressed. Methods for construction of nucleic acid molecules encoding a (poly)peptide/protein according to the present disclosure, for construction of vectors comprising said nucleic acid molecules, for introduction of said vectors into appropriately chosen host cells, for causing or allowing the expression of (poly)peptides/proteins are well-known in the art (see, e.g., Sambrook et al., 1989; Ausubel et al., 1999). Further well-known are methods for the introduction of genetic material required for the generation of progeny bacteriophages or bacteriophage particles in appropriate host cells, and for causing or allowing the generation of said progeny bacteriophages or bacteriophage particles (see, e.g., Kay et al., 1996). The step of causing or allowing the production of bacteriophage particles may require the use of appropriate helper phages, e.g. in the case of working with phagemids.

In another embodiment, the present disclosure relates to a vector comprising a nucleic acid sequence according to the present disclosure.

In a further embodiment, the present disclosure relates to a host cell containing a nucleic acid sequence according to the present disclosure or a vector according to the present disclosure.

In the context of the present disclosure the term "host cell" may be any of a number commonly used in the production of heterologous proteins, including but not limited to bacteria, such as *Escherichia coli* (Ge et al., 1995), or *Bacillus subtilis* (Wu et al., 1993), fungi, such as yeasts (Horwitz et al., 1988; Ridder et al., 1995) or filamentous fungus (Nyyssönen et al., 1993), plant cells (Hiatt & Ma, 1993; Whitelam et al., 1994), insect cells (Potter et al., 1993; Ward et al., 1995), or mammalian cells (Trill et al., 1995).

In a yet further preferred embodiment, the present disclosure relates to a modified variant of a wild type bacteriophage coat protein encoded by a nucleic acid sequence according to the present disclosure, a vector according to the present disclosure or produced by a host cell according to the present disclosure. The modified variant may further comprise amino acid residues required for cloning, for expression, or protein transport. Amino acid residues required for cloning may include residues encoded by nucleic acid sequences comprising recognition sequences for restriction endonucleases which are incorporated in order to enable the cloning of the nucleic acid sequences into appropriate vectors. Amino acid residues required for expression may include residues leading to increased solubility or stability of the (poly)peptide/protein. Amino acid residues required for protein transport may include signalling sequences responsible for the transport of the modified variant to the periplasm of E. coli, and/or amino acid residues facilitating the efficient cleavage of said signalling sequences. Further amino acid residues required for cloning, expression, protein transport, purification and/or detection purposes referred to above are numerous moieties well known to the practitioner skilled in the art.

A "diverse collection of bacteriophage particles" may as well be referred to as a "library" or a "plurality". In the context of the present disclosure, each member of such a library displays a distinct member of the library. In the context of the present disclosure the term "diverse collection" refers to a collection of at least two particles or molecules which differ in at least part of their compositions, properties, and/or sequences. For example, a diverse collection of cyclic peptides is a set of cyclic peptides which differ in at least one amino acid position of their sequence. Such a diverse collection can be obtained in a variety of ways, for example by random mutagenesis of at least one codon of a nucleic acid sequence encoding a starting (poly)peptide/protein, by using error-prone PCR to amplify a nucleic acid sequence encoding a starting (poly)peptide/protein, or by using mutator strains as host cells in a method according to the present disclosure. These and additional or alternative methods for the generation of diverse collections of peptides are well-known to one of ordinary skill in the art.

In the context of the present disclosure the term "desired property" refers to a predetermined property which one member out of the diverse collection should have and which forms the basis for screening and/or selecting the diverse collection. Such properties comprise properties such as binding to a target, blocking of a target, activation of a target-mediated reaction, enzymatic activity, and further properties which are known to one of ordinary skill. Depending on the type of desired property, one of ordinary skill will be able to identify format and necessary steps for performing screening and/or selection.

Most preferred is a method, wherein said desired property is binding to a target of interest.

Said target of interest can be presented to said diverse collection of cyclic peptides displayed on bacteriophage particles in a variety of ways well known to one of ordinary skill, such as coated on surfaces for solid phase biopanning, linked to particles such as magnetic beads for biopanning in solution, or displayed on the surface of cells for whole cell biopanning or biopanning on tissue sections. Bacteriophage particles having bound to said target can be recovered by a variety of methods well known to one of ordinary skill, such as by elution with appropriate buffers, either by using a pH- or salt gradient, or by specific elution using soluble target.

The term "in the vicinity of" refers to a stretch of up to 15, or more preferably, up to 10 amino acids, counted in both cases from either N- or C-terminus of said (poly) peptide/protein

DETAILED DESCRIPTION AND EMBODIMENTS

The present disclosure relates to a method for displaying a cyclic peptide on the surface of a bacteriophage particle, wherein said cyclic peptide is attached to the C-terminus of a coat protein of said bacteriophage particle and wherein said cyclic peptide comprises an intramolecular bond formed by coupling of one or more dehydrated residues to a cysteine or a lysine.

In one embodiment the present disclosure relates to a method for displaying a cyclic peptide on the surface of a bacteriophage particle comprising the following steps:

(a) providing a host cell harbouring a nucleic acid sequence comprising a nucleic acid sequence encoding a precursor cyclic peptide;

(b) causing or allowing the expression of said precursor cyclic peptide;

(c) enzymatic dehydration of one or more amino acid residues within the precursor cyclic peptide;

(d) forming of one or more intramolecular bonds by coupling of one or more dehydrated residues to a cysteine or a lysine, thereby forming a cyclic peptide; and (e) producing bacteriophage particles in said host cell, wherein said bacteriophage particles display said cyclic peptide on the surface and wherein said cyclic peptide is attached to the C-terminus of a coat protein of said bacteriophage particles.

In one embodiment the present disclosure relates to a method for displaying a cyclic peptide on the surface of a bacteriophage particle comprising the following steps:

(a) providing a host cell harbouring a nucleic acid sequence encoding a precursor cyclic peptide;

(b) causing or allowing the expression of said precursor cyclic peptide;

(c) causing or allowing the enzymatic dehydration of one or more amino acid residues within the precursor cyclic peptide;

(d) causing or allowing the formation of one or more intramolecular bonds by coupling of one or more dehydrated residues to a cysteine or a lysine, thereby forming a cyclic peptide; and (e) producing bacteriophage particles in said host cell, wherein said bacteriophage particles display said cyclic peptide on the surface and wherein said cyclic peptide is attached to the C-terminus of a coat protein of said bacteriophage particles.

In one embodiment of the present disclosure said nucleic acid sequence further encodes a coat protein of a bacteriophage particle and a leader sequence which is recognized by a post-translationally modifying (PTM) enzyme.

In one embodiment of the present disclosure the host cell further harbours one or more nucleic acid sequences encoding a post-translationally modifying (PTM) enzyme. In another embodiment of the present disclosure the host cell further harbours one or more nucleic acid sequences encoding a post-translationally modifying (PTM) enzyme, wherein said one or more nucleic acid sequences were artificially introduced into the cell.

In one embodiment the present disclosure relates to a method for displaying a cyclic peptide on the surface of a bacteriophage particle comprising the following steps:

(a) providing a host cell harbouring a nucleic acid sequence encoding a precursor cyclic peptide and harbours one or more nucleic acid sequences encoding a post-translationally modifying (PTM) enzyme;

(b) causing or allowing the expression of said precursor cyclic peptide and said one or more post-translationally modifying (PTM) enzymes;

(c) enzymatic dehydration of one or more amino acid residues within the precursor cyclic peptide;

(d) forming of one or more intramolecular bonds by coupling of one or more dehydrated residues to a cysteine or a lysine, thereby forming a cyclic peptide; and (e) producing bacteriophage particles in said host cell, wherein said bacteriophage particles display said cyclic peptide on the surface and wherein said cyclic peptide is attached to the C-terminus of a coat protein of said bacteriophage particles.

In one embodiment the present disclosure relates to a method for displaying a cyclic peptide on the surface of a bacteriophage particle comprising the following steps:

(a) providing a host cell harbouring a nucleic acid sequence encoding a precursor cyclic peptide harbours one or more nucleic acid sequences encoding a post-translationally modifying (PTM) enzyme;

(b) causing or allowing the expression of said precursor cyclic peptide and said one or more post-translationally modifying (PTM) enzymes;

(c) causing or allowing the enzymatic dehydration of one or more amino acid residues within the precursor cyclic peptide;

(d) causing or allowing the formation of one or more intramolecular bonds by coupling of one or more dehydrated residues to a cysteine or a lysine, thereby forming a cyclic peptide; and (e) producing bacteriophage particles in said host cell, wherein said bacteriophage particles display said cyclic peptide on the surface and wherein said cyclic peptide is attached to the C-terminus of a coat protein of said bacteriophage particles.

In one embodiment the enzymatic dehydration in step c) is caused by a post-translationally modifying (PTM) enzyme. In one embodiment the forming of one or more intramolecular bonds in step d) is caused by a post-translationally modifying (PTM) enzyme. In one embodiment the enzymatic dehydration in step c) and the forming of one or more intramolecular bonds in step d) is caused by a post-translationally modifying (PTM) enzyme. In one embodiment the enzymatic dehydration in step c) and the forming of one or more intramolecular bonds in step d) is caused by one post-translationally modifying (PTM) enzyme. In another embodiment the enzymatic dehydration in step c) and the forming of one or more intramolecular bonds in step d) is caused by different post-translationally modifying (PTM) enzymes. In another embodiment the enzymatic dehydration in step c) is caused by a post-translationally modifying (PTM) enzyme and the one or more intramolecular bonds in step d) are formed under basic conditions. In yet another embodiment the enzymatic dehydration in step c) is caused by a post-translationally modifying (PTM) enzyme and the one or more intramolecular bonds are formed under basic conditions after the production of bacteriophage particles in the host cell.

In one embodiment of the present disclosure said post-translationally modifying (PTM) enzyme is a lanthipeptide synthetase. In another embodiment of the present disclosure said post-translationally modifying (PTM) enzyme is a dehydratase, cyclase or a bi- or multifunctional enzyme comprising dehydratase or lyase/kinase and cyclase activity. In a preferred embodiment the PTM enzymes used herein are LanB type dehydratases, LanC type cyclases, bifunctional LanM type enzymes or multifunctional LanKC or LanL type enzymes or a functional equivalent thereof. In another embodiment of the present disclosure said post-translationally modifying (PTM) enzyme is a dehydratase or a lyase/kinase and/or a cyclase.

In one embodiment of the present disclosure said one or more dehydrated residues are dehydroalanines (Dha) or dehydrobutyrines (Dhb).

In one embodiment of the present disclosure the one or more intramolecular bonds are formed by a lanthipeptide synthetase or under mild basic conditions. In another embodiment of the present disclosure the one or more intramolecular bonds are formed by a LanC type cyclase, a bifunctional LanM type enzyme or a multifunctional LanKC or LanL type enzyme or under mild basic conditions. In one embodiment of the present disclosure the dehydration of amino acid residues and the formation of an intramolecular bond is mediated by lanthionine- or methyllanthionine-bridge forming enzymes.

In an embodiment of the present disclosure the one or more intramolecular bonds are formed within a peptide or polypeptide sequence. In an embodiment of the present disclosure the intramolecular bonds within a peptide or polypeptide sequence form a stabilizing ring structure. In one embodiment of the present disclosure the one or more intramolecular bonds are formed within post-translationally modified peptides or polypeptides. In one embodiment of the present disclosure the one or more intramolecular bonds are formed within a peptide or polypeptide comprising one or more dehydrated residues. In another embodiment the one or more intramolecular bonds are formed within a peptide or polypeptide that was modified by a lanthipeptide synthetase. In another embodiment the one or more intramolecular bonds are formed within a peptide or polypeptide that was modified by a dehydratase, cyclase or a bi- or multifunctional enzyme comprising dehydratase or lyase/kinase and cyclase activity. In another embodiment the one or more intramolecular bonds are formed within a peptide or polypeptide that was modified by a LanB type dehydratase, a LanC type cyclase, a bifunctional LanM type enzyme or a multifunctional LanKC or LanL type enzyme. In another embodiment the LanB type dehydratase is NisB (Uniprot accession number: P20103), EpiB, SpaB, MibB, PepB or a functional equivalent thereof. In a further embodiment said bifunctional LanM type enzyme is ProcM from *Prochlorococcus* MIT 9313 (Accession number NP_894083) or its closely related analogue ProcM from *Prochlorococcus* MIT 9303 (Accession number YP_001018107), CyanM1-4 (Accession numbers YP_002485891, YP_002483601, YP_002484655, YP_002483742; from *Cyanothece* sp. PCC 7425), LctM, MutM, BovM, LanM1/2, CinM, HalM1/2, or a functional equivalent thereof.

In one embodiment said one or more intramolecular bonds are formed by lanthionine- or methyllanthionine-bridge forming enzymes. In one embodiment said one or more intramolecular bonds are formed by a cyclase. In one embodiment said cyclase is a LanC type cyclase, a bifunctional LanM type enzyme or a multifunctional LanKC or LanL type enzyme.

In another embodiment the LanC type cyclase is NisC (Uniprot accession number: Q03202), SpaC, MibC, PepC, EpiC or a functional equivalent thereof. In a further embodiment said bifunctional LanM type enzyme is ProcM from *Prochlorococcus* MIT 9313 (Accession number NP_894083) or its closely related analogue ProcM from *Prochlorococcus* MIT 9303 (Accession number YP_001018107), CyanM1-4 (Accession numbers YP_002485891, YP_002483601, YP_002484655, YP_002483742; from *Cyanothece* sp. PCC 7425), LctM, MutM, BovM, LanM1/2, CinM, HalM1/2, or a functional equivalent thereof.

In another embodiment said one or more intramolecular bonds are formed under mild basic conditions. In another embodiment said mild basic conditions are at a pH between 7.5 and 11, between 8 and 11, between 9 and 11, between 10 and 11, between 7.5 and 9, between 8 and 9 or between 9 and 10. In another embodiment said mild basic conditions are at pH7.5, pH8, pH8.5, pH9, pH9.5, pH10, pH10.5 or pH11 or a range between each of them.

In another embodiment of the present disclosure the one or more intramolecular bonds are thioether-bridges. In another embodiment of the present disclosure the one or more intramolecular bonds are lanthionine-bridges or methyllanthionine-bridges. In another embodiment of the present disclosure the one or more intramolecular bonds are lysinoalanine-bridges.

In one embodiment of the present disclosure the cyclic peptide is a post-translationally modified peptide or polypeptide. In another embodiment the cyclic peptide is a thioether-bridge containing peptide or polypeptide. In another embodiment the cyclic peptide is a lanthionine-bridge containing peptide or polypeptide, a methyllanthionine-bridge containing peptide or polypeptide or a lysinoalanine-bridge containing peptide or polypeptide. In another embodiment of the present disclosure the cyclic peptide is monocyclic or polycyclic.

In one embodiment the present disclosure refers to a method for displaying a cyclic peptide on the surface of a bacteriophage particle, wherein said cyclic peptide is attached to the C-terminus of a coat protein of said bacteriophage particle and wherein said cyclic peptide comprises an intramolecular bond formed by coupling of one or more dehydrated residues to a cysteine or a lysine, the method comprising the following steps:

(a) providing a host cell harbouring a nucleic acid sequence comprising a nucleic acid sequence encoding a precursor cyclic peptide;
(b) causing or allowing the expression of said precursor cyclic peptide;
(c) forming of one or more intramolecular bonds; and
(d) producing of bacteriophage particles in said host cell.

In one embodiment of the present disclosure said coat protein is a wild type coat protein of a bacteriophage. In another embodiment said coat protein of the bacteriophage particle is or is derived from the wild type coat protein pIII or the wild type coat protein pVIII.

In one embodiment of the present disclosure said cyclic peptide is attached to the C-terminus of a coat protein of said bacteriophage particle. In another embodiment said cyclic peptide and the C-terminus of a coat protein of said bacteriophage particle are physically associated. In another embodiment said cyclic peptide is attached at to the C-terminus of a coat protein of said bacteriophage particle via genetic fusion or via a disulphide bond formed by one or more artificially introduced cysteines.

In one embodiment of the present disclosure said cyclic peptide is attached to the C-terminus of a coat protein of said bacteriophage particle via genetic fusion or via a disulphide bond formed by one or more artificially introduced cysteines. In another embodiment said cyclic peptide is attached to the C-terminus of a coat protein of said bacteriophage particle via genetic fusion. In another embodiment of the present disclosure said cyclic peptide is attached to the C-terminus of a coat protein of said bacteriophage particle via a disulphide bond formed by one or more artificially introduced cysteines.

In one embodiment of the present disclosure said bacteriophage is a filamentous bacteriophage.

In one embodiment of the present disclosure said cyclic peptide comprises up to 500, up to 400, up to 300, up to 200, up to 100, up to 90, up to 80, up to 70, up to 60, up to 50, up to 40, up to 30, up to 20, or up to 10 amino acids.

In another embodiment of the present disclosure said cyclic peptide is an amidated cyclic peptide. In a further embodiment said amidated cyclic peptide comprises an amide moiety at the C-terminus of said cyclic peptide In another embodiment of the present disclosure said cyclic peptide is post-translationally modified by C-terminal amidation. In another embodiment the amino acid to be modified for amidation is followed by a glycine, which provides the amide group. The amidation for example includes a first reaction step in which the glycine is oxidized to form alpha-hydroxy-glycine. The oxidized glycine cleaves into the C-terminally amidated peptide and an N-glyoxylated peptide. C-terminal amidation can be essential to the biological activity of many peptides, such as neuropeptides and hormones.

In one embodiment the present disclosure refers to a nucleic acid sequence capable of displaying a cyclic peptide on the surface of a bacteriophage particle, wherein the nucleic acid encodes
(a) a coat protein of said bacteriophage particle,
(b) a leader sequence which is recognized by a post-translationally modifying (PTM) enzyme, and
(c) a precursor cyclic peptide,
wherein the precursor cyclic peptide is located at the C-terminus of the coat protein of said bacteriophage particle, and
wherein said precursor cyclic peptide is able to form an intramolecular bond by coupling of one or more dehydrated residues to a cysteine or a lysine.

In one embodiment the present disclosure said nucleic acid sequence capable of displaying a cyclic peptide on the surface of a bacteriophage particle further encodes a signal sequence.

In one embodiment the present disclosure refers to a vector comprising a nucleic acid sequence capable of displaying a cyclic peptide on the surface of a bacteriophage particle, wherein the nucleic acid encodes
(a) a coat protein of said bacteriophage particle;
(b) a leader sequence which is recognized by a post-translationally modifying (PTM) enzyme, and
(c) a precursor cyclic peptide,
wherein the precursor cyclic peptide is located at the C-terminus of the coat protein of said bacteriophage particle, and
wherein said precursor cyclic peptide is able to form an intramolecular bond by coupling of one or more dehydrated residues to a cysteine or a lysine.

In one embodiment the present disclosure refers to a nucleic acid sequence capable of displaying a cyclic peptide on the surface of a bacteriophage particle, wherein the nucleic acid has the following arrangement from the N-terminus to C-terminus:
N-(phage coat protein)-(leader sequence recognized by a post-translationally modifying (PTM) enzyme)-(precursor cyclic peptide)-C.

In one embodiment the present disclosure refers to a vector comprising a nucleic acid sequence capable of displaying a cyclic peptide on the surface of a bacteriophage particle, wherein the nucleic acid has the following arrangement from the N-terminus to C-terminus:

N-(phage coat protein)-(leader sequence recognized by a post-translationally modifying (PTM) enzyme)-(precursor cyclic peptide)-C, wherein N is the N-terminus and C is the C-terminus.

In one embodiment the present disclosure refers to a nucleic acid sequence capable of displaying a cyclic peptide on the surface of a bacteriophage particle, wherein the nucleic acid has the following arrangement from the N-terminus to C-terminus:

N-(signal sequence)-(phage coat protein)-(leader sequence recognized by a post-translationally modifying (PTM) enzyme)-(precursor cyclic peptide)-C.

In one embodiment the present disclosure refers to a vector comprising a nucleic acid sequence capable of displaying a cyclic peptide on the surface of a bacteriophage particle, wherein the nucleic acid has the following arrangement from the N-terminus to C-terminus:

N-(signal sequence)-(phage coat protein)-(leader sequence recognized by a post-translationally modifying (PTM) enzyme)-(precursor cyclic peptide)-C, wherein N is the N-terminus and C is the C-terminus.

In another embodiment of the present disclosure a vector further comprises one or more nucleic acid sequences encoding an export signal. In another embodiment of the present disclosure a vector further comprises one or more nucleic acid sequences encoding an inducible promoter. In one embodiment the present disclosure refers to a host cell comprising nucleic acid sequences or vectors as disclosed herein.

In another embodiment the present disclosure refers to a vector comprising a nucleic acid sequence capable of displaying a cyclic peptide on the surface of a bacteriophage particle wherein the nucleic acid encodes a phage coat protein wherein said phage coat protein is encoded in the vicinity of the leader sequence recognized by a post-translationally modifying (PTM) enzyme.

In another embodiment the present disclosure refers to a vector comprising a nucleic acid sequence capable of displaying a cyclic peptide on the surface of a bacteriophage particle wherein leader sequence recognized by a post-translationally modifying (PTM) enzyme is encoded in the vicinity of the precursor cyclic peptide.

In a further embodiment the present disclosure refers to a vector comprising a nucleic acid sequence wherein on said nucleic acid sequence the phage coat protein is encoded in the vicinity of the leader sequence recognized by a post-translationally modifying (PTM) enzyme and said leader sequence is encoded in the vicinity of the precursor cyclic peptide. In an embodiment of the present disclosure in the vicinity refers to 15, 14, 13, 12, 11, 10, 9, 8, 7, 6, 5, 4, 3, 2 or 1 amino acids encoded by corresponding triplets of nucleic acids.

In another embodiment said precursor cyclic peptide comprises at least one or more serines or threonines and one or more cysteines or lysines to form one or more intramolecular bonds. In another embodiment said coat protein of the bacteriophage particle encoded by a nucleic acid is or is derived from the wild type coat protein pIII or the wild type coat protein pVIII.

In one embodiment the present disclosure refers to a bacteriophage particle displaying a cyclic peptide on its surface obtainable by a method as disclosed herein. In one embodiment the present disclosure refers to a bacteriophage particle displaying a cyclic peptide on its surface, wherein said cyclic peptide is attached to the C-terminus of a coat protein of said bacteriophage particle and wherein said cyclic peptide comprises an intramolecular bond. In one embodiment the present disclosure refers to a bacteriophage particle displaying a cyclic peptide on its surface, wherein said cyclic peptide is attached to the C-terminus of a coat protein of said bacteriophage particle and wherein said cyclic peptide comprises an intramolecular bond formed by coupling of one or more dehydrated residues to a cysteine or a lysine.

In another embodiment said bacteriophage particle further comprises a vector comprising one or more nucleic acid sequences encoding a precursor cyclic peptides able to form said cyclic peptide. In another embodiment said bacteriophage particle comprises a vector as disclosed herein.

In one embodiment the present disclosure refers to a diverse collection of bacteriophage particles as disclosed herein. In one embodiment the present disclosure refers to a diverse collection of bacteriophage particles wherein said bacteriophage particles display a cyclic peptide which is attached to the C-terminus of a coat protein of said bacteriophage particle and wherein said cyclic peptide comprises an intramolecular bond. In another embodiment each of said bacteriophage particles displays a cyclic peptide out of a diverse collection of cyclic peptides wherein said cyclic peptides comprise an intramolecular bond. In one embodiment the present disclosure refers to a diverse collection of bacteriophage particles wherein said bacteriophage particles display a cyclic peptide which is attached to the C-terminus of a coat protein of said bacteriophage particle and wherein said cyclic peptide comprises an intramolecular bond formed by coupling of one or more dehydrated residues to a cysteine or a lysine. In another embodiment each of said bacteriophage particles displays a cyclic peptide out of a diverse collection of cyclic peptides wherein said cyclic peptides comprise an intramolecular bond formed by coupling of one or more dehydrated residues to a cysteine or a lysine.

In one embodiment the present disclosure refers to a method for obtaining a cyclic peptide having a desired property, comprising:

(a) providing a diverse collection of bacteriophage particles as disclosed herein; and (b) screening said diverse collection and/or selecting from said diverse collection to obtain at least one bacteriophage particle displaying a cyclic peptide having said desired property.

In one embodiment the present disclosure refers to a method for obtaining a cyclic peptide having a desired property, comprising:

(a) providing a diverse collection of bacteriophage particles wherein said bacteriophage particles display a cyclic peptide that is attached to the C-terminus of a coat protein of said bacteriophage particle and wherein said cyclic peptide comprises an intramolecular bond formed by coupling of one or more dehydrated residues to a cysteine or a lysine; and (b) screening said diverse collection and/or selecting from said diverse collection to obtain at least one bacteriophage particle displaying a cyclic peptide having said desired property.

In one embodiment of the present disclosure said desired property is binding to a target of interest.

In another embodiment the present disclosure refers to a method for obtaining a cyclic peptide having a desired property, comprising:

(a) providing a diverse collection of bacteriophage particles wherein said bacteriophage particles display a cyclic peptide that is attached to the C-terminus of a coat protein of said bacteriophage particle and wherein said cyclic peptide comprises an intramolecular bond formed by coupling of one or more dehydrated residues to a cysteine or a lysine; and (b) screening said diverse collection and/or selecting from said diverse collection to obtain at least one bacteriophage particle displaying a cyclic peptide having said desired property, wherein step (b) further comprises:

(ba) contacting said diverse collection of bacteriophage particles with the target of interest;

(bb) eluting bacteriophage particles not binding to the target of interest; and (bc) eluting bacteriophage particles binding to the target of interest.

In one embodiment the present disclosure refers to a method for obtaining a cyclic peptide having a desired property, comprising:

(a) providing a diverse collection of bacteriophage particles wherein said bacteriophage particles display a cyclic peptide out of a diverse collection of cyclic peptides that is attached to the C-terminus of a coat protein of said bacteriophage particle and wherein said cyclic peptide comprises an intramolecular bond formed by coupling of one or more dehydrated residues to a cysteine or a lysine; and (b) screening said diverse collection and/or selecting from said diverse collection to obtain at least one bacteriophage particle displaying a cyclic peptide having said desired property.

In one embodiment of the present disclosure said desired property is binding to a target of interest.

In another embodiment the present disclosure refers to a method for obtaining a cyclic peptide having a desired property, comprising:

(a) providing a diverse collection of bacteriophage particles wherein said bacteriophage particles display a cyclic peptide out of a diverse collection of cyclic peptides that is attached to the C-terminus of a coat protein of said bacteriophage particle and wherein said cyclic peptide comprises an intramolecular bond formed by coupling of one or more dehydrated residues to a cysteine or a lysine; and (b) screening said diverse collection and/or selecting from said diverse collection to obtain at least one bacteriophage particle displaying a cyclic peptide having said desired property, wherein step (b) further comprises:

(ba) contacting said diverse collection of bacteriophage particles with the target of interest;

(bb) eluting bacteriophage particles not binding to the target of interest; and (bc) eluting bacteriophage particles binding to the target of interest.

The Lan-Enzymes

Currently several lanthionine- or methyllanthionine-bridge forming enzymes and their genes are known:

1. LanB type dehydratases are shown to constitute the C-terminus of the enzyme proposed to catalyse the dehydration step of serine and threonine.
2. LanC type cyclases catalyse the addition of cysteine thiols. LanC, the cyclase component, is a zinc metalloprotein, whose bound metal has been proposed to activate the thiol substrate for nucleophilic addition.
3. LanM type enzymes are bifunctional dehydratases and cyclases. It is responsible for both the dehydration and the cyclization of the precursor-peptide during lantibiotic synthesis.
4. LanD oxidative decarboxylase type enzymes catalyze the removal of two reducing equivalents from the cysteine residue of the C-terminal meso-lanthionine of epidermin to form a ~C═C~ double bond.
5. LanKC type multifunctional enzymes that contain lyase, kinase, and cyclase domains, but lack the signature zinc-ligands in the cyclase domain.
6. LanL type multifunctional enzymes that contain lyase, kinase, and a metal ligand containing cyclase domain.
7. LanP type peptidases are cleaving the leader peptide from the lantibiotics.
8. LanT type peptidase fused to an ABC transporter; the cleavage of precursor peptide is mediated by the transporter as part of the secretion process.
9. LtnM and LtnJ type of dehydratase and dehydrogenase are involved in the formation of D-alanine.
10. CinX hydroxylates asparagines during the cinnamycin biosynthesis.

For example, in the formation of lantibiotics (antimicrobial peptides comprising a lanthionine-bridge or a methyllanthionine-bridge) the lantibiotic-synthesizing enzymes have been described as being organized in a membrane-bound complex (Siegers et al. 1996. J. Biol. Chem. 271, 12294-12301; Kiesau et al. 1997. J. Bacteriol. 179, 1475-1481; Sahl et al. 1998. Annu. Rev. Microbiol. 52:41-7). Such complex is composed of the lantibiotic transporter (LanT), the dehydrating enzyme (LanB; also referred to as dehydratase) and the cyclase (LanC). In the case of some lantibiotics a bifunctional enzyme (LanM) performs both the dehydration and the cyclization steps. The N-terminal lantibiotic leader peptide in the ribosomally synthesized precursor peptides is a recognition signal for the lantibiotic enzymes, starting with the dehydrating enzyme or the enzyme which performs both dehydration and ring formation. It is thought that the leader peptide binds to the lantibiotic complex to bring the precursor peptide in close proximity of the lantibiotic enzymes. The prior art (see e.g. WO2006/062398) discloses several lantibiotic leader peptides and their uses, e.g. in fusion proteins to produce a peptide of interest which is to be post-translationally dehydrated by a dehydratase. According to WO2006/062398, the leader peptide and peptide to be modified are preceded by a non-lantibiotic export signal, like the SEC export signal. The export signal and leader peptide may be separated by a cell anchor sequence, for instance an LPTX-sortase recognition motif.

Genome mining strategies can be employed by a skilled person to identify novel leader peptides and their cognate modifying Lan-enzyme(s), as recently described in detail (Qi Zhang, Xiao Yang, Huan Wang, Wilfred A. van der Donk (2014) ACS Chem. Biol., 2014, 9, 2686-2694). Lan-enzymes are characterized by sequence similarities, similar domain structures, and highly conserved motifs. For example several Lan-enzymes known to date, contain a "CHG" motif in the cyclase domain that supports binding of an active site zinc ion. Others were identified to contain a "CCG" motif that supports $Zn^{2+}$ coordination. Using Lan-enzyme sequences and conserved motifs as a query novel Lan-enzymes can be identified in other organisms by BlastP searches. Once a novel Lan-enzyme is identified, their cognate substrate LanA precursor peptides are easily detected, since they are usually encoded nearby in the same genomic cluster and characterized by short open reading frames and sequence similarities to other LanAs.

The Leader Sequence

Any type of leader sequence can be used for practising the present disclosure, provided that it can be recognized by a dehydratase. In another embodiment such leader sequence is also recognized by a cyclase that can form a lanthionine- or methyllanthionine-bridge. Amino acid sequences of leader sequences are available from public databases and publications, including leader sequences and leader consensus sequences as described in Plat A. et al. 2013 Curr Protein Pept Sci. 2013 March; 14(2):85-96 and Plat A. et al.; Appl Environ Microbiol. 2011 January; 77(2):604-11.

In one embodiment said leader sequence is a leader sequence or bears a consensus motif thereof which is recognized by a LanB type dehydratase, a LanC type cyclase, a bifunctional LanM type enzyme or a multifunctional LanKC or LanL type enzyme.

In another embodiment, a leader sequence of the disclosure bears a leader sequence from a LanA precursor peptide or a consensus motif that can be derived from the amino acid sequence alignment of known leader sequences derived from LanA precursor peptides. In a further embodiment said leader sequence is a leader sequence from a LanA precursor peptide or is a leader sequence derived from a LanA precursor peptide or is a leader sequence which bears a consensus motif from LanA precursor peptides and wherein said leader sequence is recognized by a lanthipeptide synthetase. In a further embodiment said leader sequence is a leader sequence from a LanA precursor peptide or is a leader sequence derived from a LanA precursor peptide or is a leader sequence which bears a consensus motif from LanA precursor peptides and wherein said leader sequence is recognized by a LanB type dehydratase, a LanC type cyclase, a bifunctional LanM type enzyme or a multifunctional LanKC or LanL type enzyme.

Amino acid sequences of LanA precursor peptides are available from public databases and include the following LanA precursor peptides:

NisA (Nisin, *Lactococcus lactis*)
ProcA (Prochlorosin, *Prochlorococcus marinus* MIT9313; *Prochlorococcus marinus* MIT9303)
SpaS (Subtilin; *Bacillus subtilis* ATCC 6633)
LctA (Lacticin 481; *Lactococcus lactis* subsp. *lactis*)
MutA (Mutacin II, *Streptococcus mutans*)
MibA (Microbisporicin, *Microbispora corallina*)
BovA (Bovicin HJ50; *Streptococcus bovis* HJ50)
LanA1/2 (Lichenicidin, *Bacillus licheniformis*)
CinA (Cinnamycin, *Streptomyces cinnamoneus cinnamoneus* DSM 40005)
HalA1/2 (Haloduracin, *Bacillus halodurans*)
CyanA (not named, *Cyanothece* sp. PCC 7425)
Pep5 (*Staphylococcus epidermidis*)
EpiA (Epidermin, *Staphylococcus epidermidis*)

Tables 1A and 1B of WO2006/062398 show exemplary alignments of such leader peptides. A skilled person will be able to derive a consensus motif from the aligned sequences, for instance using publicly or commercially available alignment software such as AlignX of Vector NTI. It is preferred that a leader sequence consensus motif is derived from an alignment of at least 5, more preferably at least 10, most preferably at least 15 known leader peptide sequences. The thus obtained consensus motif can subsequently be verified for leader peptide activity, i.e. recognition by a dehydratase and serine or threonine dehydration, using methods known in the art. Dehydration of a given target sequence, can be monitored using Maldi-TOF MS.

The leader peptide consensus sequence can comprise various consensus sequences, for instance the consensus motif X1-D/E-E-V/L-S/T-D/E-X2-E-L-D/E, wherein X1 is any hydrophobic amino acid and wherein X2 is any amino acid. For example, it comprises the sequence LEEVSEQELD (SEQ-ID.: 7). In another embodiment, a leader sequence comprises a consensus motif F-D/E/N-L-D/E/N-X3, wherein X3 is L, I or V. For example, it comprises the sequence LFDLDL (SEQ-ID.: 8) or FNLDV (SEQ-ID.: 9). The leader may for instance also contain the consensus I/L-L/F-D/E/N-L-Q-D/N/A/S/T-L/M-D/E comprising ILELQNLD (SEQ-ID.: 10). The leader peptide may be composed of the consensus sequence e.g. FNLDV (SEQ-ID.: 9) followed by a spacer sequence between the consensus sequence and the precursor peptide to be modified. This spacer sequence brings the part to be modified within reach of the catalytic centre of the respective enzymes (Annechien Plat, Leon D. Kluskens, Anneke Kuipers, Rick Rink, Gert N. Moll (2010). The N-terminal domain and a spacer are sufficient for functionality of the nisin leader peptide. Appl. Environ. Microbiol. 77, 604-611).

Many class II LanA leader peptides are assigned to the N11P, TIGR03898, and N11P families based on sequence similarities, whereas other members currently lack a family assignment. In another embodiment, a leader sequence is derived from a ProcA leader, which currently comprises 29 highly conserved members encoded in *Prochlorococcus* MIT 9313, and another 15 members encoded in *Prochlorococcus* MIT 9303, all of which are assigned to the N11P family of leader peptides and are the substrates of a single modifying ProcM enzyme encoded in the cognate strains. Most ProcA leader sequences are remarkably long (exceeding 60 amino acids) and have no clear-cut minimal consensus sequence due to the overall high conservation. However, N-terminal truncation of the parental 63 residue leader sequence of ProcA2.8 to a 23 residue version fully supports ProcM-mediated enzymatic precursor peptide modification, which indicates that large parts of the leader sequence are dispensable and that functional minimal sequences can be readily derived.

In another embodiment the leader sequence is a NisA (Nisin, *Lactococcus lactis*) or a ProcA (Prochlorosin, *Prochlorococcus marinus* MIT9313 or *Prochlorococcus marinus* MIT9303) leader sequence or bears a consensus motif that can be derived from the NisA or ProcA leader sequence.

Further embodiments disclosed herein:

1. A method for displaying a cyclic peptide on the surface of a bacteriophage particle comprising the following steps:
   (a) providing a host cell harbouring a nucleic acid sequence encoding a precursor cyclic peptide;
   (b) causing or allowing the expression of said precursor cyclic peptide;
   (c) enzymatic dehydration of one or more amino acid residues within the precursor cyclic peptide;
   (d) forming one or more intramolecular bonds by coupling of said one or more dehydrated residues to a cysteine or a lysine, thereby forming a cyclic peptide; and
   (e) producing bacteriophage particles in said host cell, wherein said bacteriophage particles display said cyclic peptide on the surface and wherein said cyclic peptide is attached to the C-terminus of a coat protein of said bacteriophage particles.

2. The method of embodiment 1, wherein said nucleic acid sequence further encodes a coat protein of a bacteriophage particle and a leader sequence which is recognized by a post-translationally modifying (PTM) enzyme.

3. The method of one of the preceding embodiments, wherein the host cell further harbours one or more nucleic acid sequences encoding a post-translationally modifying (PTM) enzyme.

4. The method of one of the embodiments 2-3, wherein said post-translationally modifying (PTM) enzyme is a lanthipeptide synthetase.

5. The method of one of the embodiments 2-4, wherein said post-translationally modifying (PTM) enzyme is a LanB type dehydratase, a LanC type cyclase and/or a bifunctional LanM type enzyme or a multifunctional LanKC or LanL type enzyme.

6. The method of one of the embodiments 2-5, wherein said leader sequence is a leader sequence from a LanA precursor peptide or is a leader sequence derived from a LanA precursor peptide or is a leader sequence which bears a consensus motif from LanA precursor peptide.

7. The method of embodiment 6, wherein said leader sequence is recognized by a LanB type dehydratase, a LanC type cyclase, a bifunctional LanM type enzyme or a multifunctional LanKC or LanL type enzyme.

8. The method of one of the embodiments 2-7, wherein said leader sequence is the NisA or a ProcA leader sequence or bears a consensus motif thereof.

9. The method of one of the preceding embodiments, wherein the one or more intramolecular bonds are formed by a cyclase or under mild basic conditions.

10. The method of one of the preceding embodiments, wherein the dehydrated residue is dehydroalanine (Dha) or a dehydrobutyrine (Dhb).

11. The method of one of the preceding embodiments, wherein the intramolecular bond is a thioether- or lysinoalanine-bridge.

12. The method of one of the preceding embodiments, wherein said coat protein is a wild type coat protein of a bacteriophage.

13. The method of embodiment 12, wherein said coat protein of the bacteriophage particle is or is derived from the wild type coat protein pIII or the wild type coat protein pVIII.

14. The method of one of the preceding embodiments, wherein said cyclic peptide is attached to the C-terminus of a coat protein of said bacteriophage particle via genetic fusion or via a disulphide bond formed by one or more artificially introduced cysteines.

15. A nucleic acid sequence capable of displaying a cyclic peptide on the surface of a bacteriophage particle, wherein the nucleic acid encodes
  (a) a coat protein of said bacteriophage particle;
  (b) a leader sequence which is recognized by a post-translationally modifying (PTM) enzyme, and
  (c) a precursor cyclic peptide,
  wherein the nucleic acid encoding the precursor cyclic peptide is located at the C terminus of the coat protein of said bacteriophage particle,
  and wherein said precursor cyclic peptide is able to form an intramolecular bond by coupling of one or more dehydrated residues to a cysteine or a lysine.

16. A nucleic acid sequence of embodiment 15 having the following arrangement from the N terminus to C-terminus:
  N-(phage coat protein)-(leader sequence recognized by a post-translationally modifying (PTM) enzyme)-(precursor cyclic peptide)-C.

17. A nucleic acid sequence of embodiments 15 to 17 wherein said leader sequence is a leader sequence from a LanA precursor peptide or is a leader sequence derived from a LanA precursor peptide or is a leader sequence which bears a consensus motif from LanA precursor peptide.

18. A nucleic acid sequence of one of the embodiments 15 to 17, wherein the precursor cyclic peptide comprises at least one or more serines or threonines and one or more cysteines or lysines.

19. A vector comprising the nucleic acid of embodiments 15 to 18.

20. A host cell comprising the nucleic acid sequence of one of the embodiments 15 to 18 or the vector of embodiment 19.

21. A bacteriophage particle displaying a cyclic peptide on its surface obtainable by a method according to one of the embodiments 1 to 14.

22. A bacteriophage particle displaying a cyclic peptide on its surface, wherein said cyclic peptide is attached to the C-terminus of a coat protein of said bacteriophage particle and wherein said cyclic peptide comprises an intramolecular bond formed by coupling of one or more dehydrated residues to a cysteine or a lysine.

23. The bacteriophage particle of embodiments 21 or 22, further comprising a vector comprising one or more nucleic acid sequences encoding a precursor cyclic peptides able to form said cyclic peptide.

24. The bacteriophage particle of embodiment 23, wherein said vector is the vector of embodiment 19.

25. A diverse collection of bacteriophage particles of any one of embodiments 21 to 24, wherein each of said bacteriophage particles displays a cyclic peptide out of a diverse collection of cyclic peptides wherein said cyclic peptides comprise an intramolecular bond formed by coupling of one or more dehydrated residues to a cysteine or a lysine.

26. A method for obtaining a cyclic peptide having a desired property, comprising:
  (a) providing the diverse collection of bacteriophage particles of embodiment 25; and
  (b) screening said diverse collection and/or selecting from said diverse collection to obtain at least one bacteriophage particle displaying a cyclic peptide having said desired property.

27. The method of embodiment 26, wherein said desired property is binding to a target of interest.

WORKING EXAMPLES

Example 1: Heterologous Expression of Soluble Thioether-Bridged Peptides in *E. coli* and Confirmation of Modification Status Using Factor Xa-Cleavage Reporter Assays In the following example, all molecular biology experiments are performed according to standard protocols (Ausubel et al., 1999).

Construction of Vectors and Soluble Expression of Model Peptides (Peptide Comprising Factor Xa-Cleaving Site):

The heterologous expression of thioether-bridged lantibiotics in *E. coli* has been recently described and was achieved by co-expression of the precursor peptides along with the cognate modifying enzymes (Shi et al., J Am Chem Soc. 2011 Mar. 2; 133(8):2338-41). We developed reporter peptides that enable the rapid assessment of their modification status in complex biological samples and only require minute amounts of material. These peptides are composed of a leader peptide (e.g. derived from NisA, ProcA, and others) fused to an artificial core peptide, which comprises a Factor Xa protease cleavage site flanked by substrate residues for enzymatic thioether-bridge installment and two affinity tags (such as $His_6$- and FLAG-tag) for detection. DNA sequences encoding these peptides were cloned under the control of an IPTG-inducible Lac-promoter into an *E. coli* expression plasmid harbouring an ampicillin resistance gene and ColE1 origin of replication. The resulting plasmids were combined with a compatible second plasmid (chloramphenicol resistance, RSF1030 origin of replication) encoding the cognate enzymes (lanthipeptide synthetases) for post-translational modification (e.g. NisB/NisC, Procto, and others) under control of an IPTG inducible $P_{LlacO1}$-promoter and were co-maintained within the same cell of *E. coli* strains. Upon IPTG co-induction in *E. coli* strains the linear precursor peptides are produced and subsequently subjected to enzyme-mediated PTM modification which leads to the covalent linkage of the substrate residues flanking the Factor Xa-cleavage site and formation of a stable thioether-bridge.

After expression, treatment of the peptides with Factor Xa protease leads to hydrolysis of the peptide bond between the arginine of the recognition site and the adjacent residue. However, instead of resulting in two separate polypeptides each containing one of the affinity tags flanking the cleavage site, the stable thioether-bridge keeps the two polypeptides including both affinity tags connected.

Accordingly, the co-detection of the two affinity tags after Factor Xa cleavage in sandwich enzyme-linked immunosorbent assays (ELISAs) can therefore be used to confirm the desired modification (cyclization) of the model peptides, whereas for unmodified peptides (linear) only one of the two tags is detectable.

The reliability of this Factor Xa-cleavage reporter assay in monitoring the modification status of model peptides is illustrated below (FIG. 1). A model peptide containing an ompA signal sequence fused to the NisA-leader peptide and a core peptide comprised of $His_6$- and FLAG-tags flanking an ASWIEGRWCN (SEQ-ID.: 1) sequence (with S and C being substrates for enzyme-mediated thioether-bridge installment; IEGR: Factor Xa recognition motif) was expressed either in absence or presence of co-expression of the modifying enzymes NisB and NisC in *E. coli* MC1061F'.

As control modification incompetent mutant peptides (S to A or C to A mutation) with otherwise same sequence were expressed in absence or presence of NisB and NisC.

All strains were grown at 37° C., 220 rpm until early logarithmic phase, peptide and enzyme expression induced by addition of 0.25 mM IPTG, and growth of the cultures continued overnight at 22° C. Cell lysates were established and the soluble protein fraction of each strain transferred in quadruplicate to anti-His IgG coated 384-well plates to capture the expressed model peptides via the $His_6$-tag. After washing (4×TBS, 1× Factor Xa reaction buffer), one of the duplicates of each sample was digested with 500 nM Factor Xa protease overnight, whereas the other duplicate was left untreated. After washing the plate with TBST biotinylated anti-FLAG IgG was added and intact peptides detected using a Streptavidin:SULFO-TAG conjugate (electrochemiluminescence was measured using an Meso Scale Discovery SECTOR Imager 6000). Signals obtained without Factor Xa treatment were set to 100% (input) and the signal ratio for the same sample after Factor Xa treatment was calculated (signal remaining after Xa-treatment [%]). Obtained values therefor reflect the percentage of Factor Xa-cleavage resistant peptide and are a direct measure of thioether-bridge formation efficacy.

As shown in FIG. 1, about 60% cleavage resistant peptide is obtained upon co-expression of the NisB and NisC enzymes, whereas peptides produced in absence of modifying enzymes are almost cleaved to completion (left panel). In contrast peptides variants containing S to A (middle panel) or C to A (right panel) mutations, which are no substrates for enzymatic thioether-bridge formation, are fully cleaved by Factor Xa even when produced in presence of NisB and NisC co-expression.

Example 2: C-Terminal Fusion of NisA-Leader Containing Precursor Peptides to pIII Supports Enzymatic Thioether-Bridge Formation in the Producer Cell and Display on Phage In most phage display applications the protein or peptide of interest is genetically fused to the N-termini of either g3p (minor coat protein pIII) or g8p (major coat protein pVIII) resulting in monovalent and polyvalent display, respectively. The N-termini of pIII and pVIII are directed away from the phage particle body which is believed to support the accessibility of the displayed protein or peptide for binding to a putative ligand of interest.

However, in addition to the widely applied display of proteins of interest on the N-termini, rare examples of phage display on the correspondent C-termini of both pIII and pVIII have been described (Fuh et al., FEBS Lett. 2000 Sep. 1; 480(2-3):231-4; Held et al., J Mol Biol. 2004 Jul. 9; 340(3):587-97.).

For display of the cyclized model peptide on phages the same NisA-leader containing model precursor peptide sequences shown in FIG. 1 were cloned into phagemid vectors as genetic fusions to both the N- and C-termini of phage g3p (N-terminal truncated variant pIII-CT) to test for enzymatic peptide modification and compatibility with display on phage particles.

We produced phage particles encoding these fusions either in presence or absence of co-expression of the cognate modifying enzymes and subjected them to Factor Xa-cleavage reporter assays.

In brief, *E. coli* MC1061F' cells harboring expression plasmids for N- or C-terminal model precursor peptide (containing the NisA-leader) fusions to pIII were grown in triplicate in presence or absence of a second expression plasmid encoding the modifying NisB and NisC enzymes. Cultures were grown in 24 well plates to early logarithmic phase at 37° C., 220 rpm, and infected with VCSM13 helper phage at a multiplicity of infection of ~10. After infection cells were harvested by centrifugation, expression of pIII-fusions and modifying enzymes induced by IPTG containing media, and phage production allowed to proceed for 16 h at 22° C. After removal of the producer cells by centrifugation the phage containing supernatant was transferred in quadruplicate to anti-M13 (Santa Cruz) IgG-coated 384 well plates to capture phage particles via the major coat protein pVIII.

After washing (4×TBS, 1× Factor Xa reaction buffer), samples of one duplicate were digested with 500 nM Factor Xa protease overnight, whereas the other duplicate was left untreated.

After washing the plate with TBST biotinylated anti-FLAG IgG (Sigma; for N-terminal pIII-fusions) or biotinylated anti-His IgG (R&D Systems; for C-terminal pIII-fusions) was added and intact peptides detected using a Streptavidin:SULFO-TAG conjugate (electrochemiluminescence was measured using an Meso Scale Discovery SECTOR Imager 6000). Signals obtained without Factor Xa treatment were set to 100% (input) and the signal ratio for the same sample after Factor Xa treatment was calculated (signal remaining after Xa-treatment [%]). Obtained values therefor reflect the percentage of Factor Xa-cleavage resistant peptide and are a direct measure of thioether-bridge formation efficacy.

As shown in FIG. 2A, co-expression of the NisB and NisC enzymes during phage production result in enzymatic thioether-bridge modification of precursor peptides fused to the C-terminus of pIII and subsequent display of cyclic peptides on the phage surface (left panel). In contrast, fusion of the same precursor peptide to the N-terminus of pIII did not result in NisB/NisC-mediated modification and no cyclic peptides could be detected on phage (right panel). This finding is further supported by results obtained using the soluble expressed Maltose-binding protein (MBP) as a precursor peptide fusion carrier, where peptide fusions to the C-terminus were enzymatically modified FIG. 2C, left panel) whereas NisB/NisC failed to modify N-terminal fusions (FIG. 2C, right panel; sample preparation and assay setup essentially as described in Example 1). In context of C-terminal precursor peptide fusions to pIII mutation of the residues involved in thioether-bridge formation, e.g. serine to alanine (pIII-NisA-Pep_A/C; FIG. 2B, left panel) or cysteine to alanine (pIII-NisA-Pep_S/A; FIG. 2B, right panel) abrogates the formation and display of cyclic peptides, which further underscores the achieved precision of tailored peptide modification.

Example 3: C-Terminal pIII Phage Display of Post Translationally Modified Peptides is Widely Applicable and can be Transferred to Other Enzymatic Systems The described approach of displaying post-translational modified peptides on the C-terminus of phage structural proteins can easily be adapted to other enzymatic or semi-enzymatic modification systems as outlined below. In another example a model precursor peptide was fused to the C-terminus of pIII (plasmid: pL3C_P3.3_mut10-His) which contains the Prochlorosin3.3 (ProcA3.3) leader peptide and the core peptide sequence GDAGIQAVLASWIEGRECNAAAGP (SEQ-ID.: 6; Factor Xa cleavage site and flanking S and C residues for post-translation modification are underlined) followed by a His$_6$-tag. In additional control constructs either the serine of the parental core peptide was mutated to threonine (to test for methyllanthionine formation via dahydrobutyrine) or the cysteine was mutated to alanine (to prevent enzymatic thioether-bridge formation).

The procM gene from *Prochlorococcus* MIT9313 encoding a bifunctional dehydratase/cyclase known to modify several natural occurring Prochlorosin (including ProcA3.3) precursors was amplified from chromosomal DNA and cloned into an *E. coli* expression plasmid. Phage displaying the model precursor peptides were produced in presence or absence of ProcM enzyme co-expression and subjected to Factor Xa-cleavage reporter assays as described above. Xa-cleavage resistant peptide fusions were detected for variants with serine/cysteine-(ProcA-Pep_S/C-pIII; FIG. 3, left panel) and threonine/cysteine-(ProcA-Pep_T/C-pIII; FIG. 3, middle panel) containing core sequence when produced in presence of the bispecific modifying ProcM enzyme, which indicates formation and display of cyclic peptides comprising lanthionines and methyllanthionines, respectively. Again, cyclic peptide formation/display was abolished when the cysteine involved in thioether-bridge formation was mutated to alanine (ProcA-Pep_S/A-pIII; FIG. 3, right panel).

Example 4: C-Terminal pIII Phage Display of Post Translationally Modified Peptides with Flexible Cycle Sizes C-terminal pIII-peptide fusions with tailored cycle sizes can be displayed on phage by adjusting the spacing of serine and threonine residues relative to the cysteine required for enzymatic modification. In another example sequences encoding model precursor peptides with increased serine to cysteine spacing were established and fused to the C-terminus of pIII. Herein, the NisA-leader peptide followed by a FLAG-tag and either ASWIEGRECN—(SEQ-ID.:11), ASWAAIEGRAECN—(SEQ-ID.:12), ASWAAA IEGRAAAECN—(SEQ-ID.:13), or ASWAAGAA IEGRAAGAAECN-motifs (SEQ-ID.:14; enabling i,i+7, i,i+10, i,i+13, and i,i+17 cycle sizes, respectively; Factor Xa cleavage site underlined), and followed by a His$_6$-tag were fused to the C-terminus of pIII. In analogy, ProcA3.3-leader peptide followed by a HA-tag and either ASW IEGRECN—(SEQ-ID.:11), ASWAA IEGRAECN—(SEQ-ID.:12), ASWAAA IEGRAAAECN—(SEQ-ID.:13), or ASWAAGAA IEGRAAGAAECN-motifs (SEQ-ID.:14), and followed by a His$_6$-tag were fused to the C-terminus of pIII. Phage displaying the model precursor peptides with NisA-, or ProcA-leader sequence were produced in presence or absence of the cognate modifying NisB/NisC or ProcM enzymes, respectively, and subjected to Factor Xa-cleavage reporter assays as described above. Factor Xa-cleavage resistant (thioether-bridged) peptide fusions displayed on phage were observed using both, the NisB/NisC (FIG. 5A) and the ProcM (FIG. 5B) enzymatic systems. As judged by the percentage of cleavage resistant peptide fusions, the modification efficacy of the tested peptides is largely independent of the cycle size.

The working examples demonstrate the enzymatic post-translational modification of leader sequence-containing peptides fused to the C-terminus of phage pIII in *E. coli* and subsequent display on phage particles. Similar results are to be expected for C-terminal precursor peptide fusions to the phage major coat protein, pVIII.

The broad applicability of the here described approach is readily apparent, since different enzymatic machinery/leader-peptide pairs originating from even distantly related species such as lactic acid- and cyanobacteria can be used effectively to install post-translational modifications. In analogy, this concept can be extended to other precursor peptide/enzymatic systems which are functionally equivalent.

In summary, the post-translational dehydration of serine and threonine residues to highly chemical reactive dehydroalanine and dehydrobutyrine, respectively, by dehydratases such as NisB or bifunctional enzymes such as ProcM and the formation of cyclic peptides by cyclases such as NisC or bifunctional enzymes such as ProcM proved to be compatible with phage display.

As an alternative under mild alkaline conditions phage displayed peptides containing dehydroalanines can be readily reacted with neighbouring cysteine or lysine residues to form thioether- and lysoalanine-bridges, respectively, to from a variety of constrained polypeptide structures displayed on phage particles.

The invention claimed is:

1. A method for displaying monocyclic and polycyclic peptides up to 500 amino acids in length on the surface of a bacteriophage particle comprising the following steps:
   (a) providing a host cell harbouring a nucleic acid sequence encoding a precursor cyclic peptide, a coat protein of a bacteriophage particle and a consensus motif which is recognized by a LanB type dehydratase, a LanC type cyclase, a bifunctional LanM type enzyme or a multifunctional LanKC or LanL type enzyme;
   (b) causing or allowing the expression of said precursor cyclic peptide, said coat protein and said consensus motif;
   (c) enzymatic dehydration of one or more amino acid residues within the precursor cyclic peptide prior to phage assembly;
   (d) forming one or more intramolecular bonds by coupling of said one or more dehydrated residues to a cysteine or a lysine, thereby forming a cyclic peptide prior to phage assembly; and
   (e) producing bacteriophage particles in said host cell, wherein said bacteriophage particles export and display said cyclic peptide on the surface, wherein said cyclic peptide is attached to the C-terminus of a coat protein of said bacteriophage particles, and wherein said cyclic peptide is selected from monocyclic peptides, polycyclic peptides with 2, 3, 4 and 5 intramolecular bonds, and cyclic peptides up to 500 amino acids in length.

2. The method of claim 1, wherein the host cell further harbours one or more nucleic acid sequences encoding a post-translationally modifying (PTM) enzyme.

3. The method of claim 1, wherein the one or more dehydrated amino acid residues are dehydroalanine (Dha) or dehydrobutyrine (Dhb).

4. The method of claim 1, wherein the intramolecular bond is a thioether- or lysinoalanine-bridge.

5. The method of claim 2, wherein said post-translationally modifying (PTM) enzyme is a lanthipeptide synthetase.

6. The method of claim 2, wherein said post-translationally modifying (PTM) enzyme is a LanB type dehydratase, a LanC type cyclase and/or a bifunctional LanM type enzyme or a multifunctional LanKC or LanL type enzyme.

* * * * *

SEQUENCE LISTING

<160> NUMBER OF SEQ ID NOS: 14

<210> SEQ ID NO 1
<211> LENGTH: 10
<212> TYPE: PRT

```
<213> ORGANISM: Artificial Sequence
<220> FEATURE:
<223> OTHER INFORMATION: Synthetic

<400> SEQUENCE: 1

Ala Ser Trp Ile Glu Gly Arg Trp Cys Asn
1               5                   10

<210> SEQ ID NO 2
<211> LENGTH: 424
<212> TYPE: PRT
<213> ORGANISM: Artificial Sequence
<220> FEATURE:
<223> OTHER INFORMATION: Synthetic

<400> SEQUENCE: 2

Met Lys Lys Leu Leu Phe Ala Ile Pro Leu Val Val Pro Phe Tyr Ser
1               5                   10                  15

His Ser Ala Glu Thr Val Glu Ser Cys Leu Ala Lys Pro His Thr Glu
            20                  25                  30

Asn Ser Phe Thr Asn Val Trp Lys Asp Asp Lys Thr Leu Asp Arg Tyr
        35                  40                  45

Ala Asn Tyr Glu Gly Cys Leu Trp Asn Ala Thr Gly Val Val Val Cys
    50                  55                  60

Thr Gly Asp Glu Thr Gln Cys Tyr Gly Thr Trp Val Pro Ile Gly Leu
65                  70                  75                  80

Ala Ile Pro Glu Asn Glu Gly Gly Ser Glu Gly Gly Ser Glu
                85                  90                  95

Gly Gly Gly Ser Glu Gly Gly Gly Thr Lys Pro Pro Glu Tyr Gly Asp
                100                 105                 110

Thr Pro Ile Pro Gly Tyr Thr Tyr Ile Asn Pro Leu Asp Gly Thr Tyr
            115                 120                 125

Pro Pro Gly Thr Glu Gln Asn Pro Ala Asn Pro Asn Pro Ser Leu Glu
            130                 135                 140

Glu Ser Gln Pro Leu Asn Thr Phe Met Phe Gln Asn Asn Arg Phe Arg
145                 150                 155                 160

Asn Arg Gln Gly Ala Leu Thr Val Tyr Thr Gly Thr Val Thr Gln Gly
                165                 170                 175

Thr Asp Pro Val Lys Thr Tyr Tyr Gln Tyr Thr Pro Val Ser Ser Lys
            180                 185                 190

Ala Met Tyr Asp Ala Tyr Trp Asn Gly Lys Phe Arg Asp Cys Ala Phe
        195                 200                 205

His Ser Gly Phe Asn Glu Asp Pro Phe Val Cys Glu Tyr Gln Gly Gln
    210                 215                 220

Ser Ser Asp Leu Pro Gln Pro Val Asn Ala Gly Gly Ser Gly
225                 230                 235                 240

Gly Gly Ser Gly Gly Gly Ser Glu Gly Gly Ser Glu Gly Gly
                245                 250                 255

Ser Glu Gly Gly Gly Ser Glu Gly Gly Ser Gly Gly Ser Gly
                260                 265                 270

Ser Gly Asp Phe Asp Tyr Glu Lys Met Ala Asn Ala Asn Lys Gly Ala
        275                 280                 285

Met Thr Glu Asn Ala Asp Glu Asn Ala Leu Gln Ser Asp Ala Lys Gly
    290                 295                 300

Lys Leu Asp Ser Val Ala Thr Asp Tyr Gly Ala Ala Ile Asp Gly Phe
305                 310                 315                 320
```

```
Ile Gly Asp Val Ser Gly Leu Ala Asn Gly Asn Ala Thr Gly Asp
            325                 330                 335

Phe Ala Gly Ser Asn Ser Gln Met Ala Gln Val Gly Asp Gly Asp Asn
        340                 345                 350

Ser Pro Leu Met Asn Asn Phe Arg Gln Tyr Leu Pro Ser Leu Pro Gln
        355                 360                 365

Ser Val Glu Cys Arg Pro Phe Val Phe Ser Ala Gly Lys Pro Tyr Glu
    370                 375                 380

Phe Ser Ile Asp Cys Asp Lys Ile Asn Leu Phe Arg Gly Val Phe Ala
385                 390                 395                 400

Phe Leu Leu Tyr Val Ala Thr Phe Met Tyr Val Phe Ser Thr Phe Ala
                405                 410                 415

Asn Ile Leu Arg Asn Lys Glu Ser
            420

<210> SEQ ID NO 3
<211> LENGTH: 73
<212> TYPE: PRT
<213> ORGANISM: Artificial Sequence
<220> FEATURE:
<223> OTHER INFORMATION: Synthetic

<400> SEQUENCE: 3

Met Lys Lys Ser Leu Val Leu Lys Ala Ser Val Ala Val Ala Thr Leu
1               5                   10                  15

Val Pro Met Leu Ser Phe Ala Ala Glu Gly Asp Asp Pro Ala Lys Ala
            20                  25                  30

Ala Phe Asn Ser Leu Gln Ala Ser Ala Thr Glu Tyr Ile Gly Tyr Ala
        35                  40                  45

Trp Ala Met Val Val Val Ile Val Gly Ala Thr Ile Gly Ile Lys Leu
    50                  55                  60

Phe Lys Lys Phe Thr Ser Lys Ala Ser
65                  70

<210> SEQ ID NO 4
<211> LENGTH: 6
<212> TYPE: PRT
<213> ORGANISM: Artificial Sequence
<220> FEATURE:
<223> OTHER INFORMATION: Synthetic

<400> SEQUENCE: 4

Leu Arg Asn Lys Glu Ser
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic

<400> SEQUENCE: 5

Thr Ser Lys Ala Ser
1               5

<210> SEQ ID NO 6
<211> LENGTH: 24
<212> TYPE: PRT
<213> ORGANISM: Artificial Sequence
<220> FEATURE:
<223> OTHER INFORMATION: Synthetic
```

```
<400> SEQUENCE: 6

Gly Asp Ala Gly Ile Gln Ala Val Leu Ala Ser Trp Ile Glu Gly Arg
1               5                   10                  15
Glu Cys Asn Ala Ala Ala Gly Pro
            20

<210> SEQ ID NO 7
<211> LENGTH: 10
<212> TYPE: PRT
<213> ORGANISM: Artificial Sequence
<220> FEATURE:
<223> OTHER INFORMATION: Synthetic

<400> SEQUENCE: 7

Leu Glu Glu Val Ser Glu Gln Glu Leu Asp
1               5                   10

<210> SEQ ID NO 8
<211> LENGTH: 6
<212> TYPE: PRT
<213> ORGANISM: Artificial Sequence
<220> FEATURE:
<223> OTHER INFORMATION: Synthetic

<400> SEQUENCE: 8

Leu Phe Asp Leu Asp Leu
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic

<400> SEQUENCE: 9

Phe Asn Leu Asp Val
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic

<400> SEQUENCE: 10

Ile Leu Glu Leu Gln Asn Leu Asp
1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic

<400> SEQUENCE: 11

Ala Ser Trp Ile Glu Gly Arg Glu Cys Asn
1               5                   10

<210> SEQ ID NO 12
<211> LENGTH: 13
<212> TYPE: PRT
<213> ORGANISM: Artificial Sequence
```

```
<220> FEATURE:
<223> OTHER INFORMATION: Synthetic

<400> SEQUENCE: 12

Ala Ser Trp Ala Ala Ile Glu Gly Arg Ala Glu Cys Asn
1               5                   10

<210> SEQ ID NO 13
<211> LENGTH: 16
<212> TYPE: PRT
<213> ORGANISM: Artificial Sequence
<220> FEATURE:
<223> OTHER INFORMATION: Synthetic

<400> SEQUENCE: 13

Ala Ser Trp Ala Ala Ala Ile Glu Gly Arg Ala Ala Ala Glu Cys Asn
1               5                   10                  15

<210> SEQ ID NO 14
<211> LENGTH: 20
<212> TYPE: PRT
<213> ORGANISM: Artificial Sequence
<220> FEATURE:
<223> OTHER INFORMATION: Synthetic

<400> SEQUENCE: 14

Ala Ser Trp Ala Ala Gly Ala Ala Ile Glu Gly Arg Ala Ala Gly Ala
1               5                   10                  15

Ala Glu Cys Asn
            20
```